US011878956B2

(12) United States Patent
Wald et al.

(10) Patent No.: US 11,878,956 B2
(45) Date of Patent: *Jan. 23, 2024

(54) METAL SALTS AND USES THEREOF

(71) Applicant: Inspirna, Inc., New York, NY (US)

(72) Inventors: Stephen Wald, Woodcliff Lake, NJ (US); Eduardo J. Martinez, Bryn Mawr, PA (US); Samuel Stratford, Cambridge (GB); Amanda Buist, Cambridge (GB); Joseph Benson, Edinburgh (GB); Jonathan Loughrey, Edinburgh (GB)

(73) Assignee: Inspirna, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/821,699

(22) Filed: Aug. 23, 2022

(65) Prior Publication Data

US 2023/0095288 A1 Mar. 30, 2023

Related U.S. Application Data

(63) Continuation of application No. 17/407,394, filed on Aug. 20, 2021, now Pat. No. 11,459,292, which is a continuation of application No. 17/119,527, filed on Dec. 11, 2020, now Pat. No. 11,174,220.

(60) Provisional application No. 62/947,968, filed on Dec. 13, 2019.

(51) Int. Cl.
  *C07C 229/34* (2006.01)
  *A61P 35/04* (2006.01)

(52) U.S. Cl.
  CPC ............ *C07C 229/34* (2013.01); *A61P 35/04* (2018.01)

(58) Field of Classification Search
  CPC ... A61P 35/04; C07B 2200/07; C07C 217/18; C07C 229/34
  See application file for complete search history.

(56) References Cited

U.S. PATENT DOCUMENTS

| | | |
|---|---|---|
| 4,683,202 A | 7/1987 | Mullis |
| 5,215,882 A | 6/1993 | Bahl et al. |
| 5,223,409 A | 6/1993 | Ladner et al. |
| 5,324,731 A | 6/1994 | Kaddurah-Daouk et al. |
| 5,530,101 A | 6/1996 | Queen et al. |
| 5,565,332 A | 10/1996 | Hoogenboom et al. |
| 5,585,089 A | 12/1996 | Queen et al. |
| 5,639,641 A | 6/1997 | Pedersen et al. |
| 5,676,978 A | 10/1997 | Teicher et al. |
| 5,707,807 A | 1/1998 | Kato |
| 5,807,522 A | 9/1998 | Brown et al. |
| 5,837,832 A | 11/1998 | Chee et al. |
| 5,843,974 A | 12/1998 | Swift |
| 5,945,289 A | 8/1999 | Lehrer |
| 5,958,342 A | 9/1999 | Gamble et al. |
| 5,994,076 A | 11/1999 | Chenchik et al. |
| 6,004,755 A | 12/1999 | Wang |
| 6,040,138 A | 3/2000 | Lockhart et al. |
| 6,048,695 A | 4/2000 | Bradley et al. |
| 6,060,240 A | 5/2000 | Kamb et al. |
| 6,087,112 A | 7/2000 | Dale |
| 6,090,556 A | 7/2000 | Kato |
| 6,316,503 B1 | 11/2001 | Li et al. |
| 6,652,860 B1 | 11/2003 | Singh et al. |
| 6,716,622 B2 | 4/2004 | Curiel et al. |
| 6,906,069 B1 | 6/2005 | Li et al. |
| 7,135,575 B2 | 11/2006 | Munson et al. |
| 7,183,295 B2 | 2/2007 | Yamazaki et al. |
| 7,247,748 B2 | 7/2007 | Thompson et al. |
| 7,365,085 B2 | 4/2008 | Bhat et al. |
| 7,476,519 B2 | 1/2009 | Monforte |
| 7,560,586 B2 * | 7/2009 | Thompson .............. C07C 47/24 560/42 |
| 7,576,215 B2 | 8/2009 | Collini et al. |
| 7,741,317 B2 | 6/2010 | Chao et al. |
| 7,790,745 B2 | 9/2010 | Yang et al. |
| 7,799,782 B2 | 9/2010 | Munson et al. |
| 7,897,750 B2 | 3/2011 | Monforte |
| 7,998,995 B2 | 8/2011 | Boren et al. |
| 8,039,493 B2 | 10/2011 | Dehmlow et al. |
| 8,236,753 B2 | 8/2012 | Blacklow et al. |
| 8,257,750 B2 | 9/2012 | Ranganathan |
| 8,324,367 B2 | 12/2012 | Kaemmerer et al. |

(Continued)

FOREIGN PATENT DOCUMENTS

| | | |
|---|---|---|
| AU | 1552599 A | 7/1999 |
| AU | 2003222083 A1 | 10/2003 |

(Continued)

OTHER PUBLICATIONS

"Definition of Cancer," MedicineNet.com, <http://www.medterms.com/script/main/art.asp?articlekey=2580&pf=3&page=1>, retrieved on Mar. 8, 2011 (2 pages).
Adeyeye et al., "Diclofenac sodium," Analytical Profiles of Drug Substances. 19:123-44 (1990) (23 pages).
Antonia et al., "Nivolumab (anti-PD-1; BMS-936558, ONO-4538) and ipilimumab in first-line NSCLC: Interim phase I results," American Society of Clinical Oncology Annual Meeting I. 32(15 suppl) Abstract 8023 (May 20, 2014).
Garzon et al., "Targeting microRNAs in cancer: rationale, strategies and challenges," available in PMC Jan. 28, 2014, published in final edited form as: Nat Rev Drug Discov. 9(10):775-789 (Oct. 2010) (26 pages).
Iclozan et al.,"Therapeutic regulation of myeloid-derived suppressor cells and immune response to cancer vaccine in patients with extensive stage small cell lung cancer," available in PMC May 1, 2014, published in final editable form as: Cancer Immunol Immunother. 62(5): 909-918 (May 2013).

(Continued)

*Primary Examiner* — Jean P Cornet
(74) *Attorney, Agent, or Firm* — Clark & Elbing LLP

(57) ABSTRACT

The present invention relates to metal salts of 2-[3-[(3R)-3-[[2-chloro-3-(trifluoromethyl)phenyl]methyl-(2,2-diphenylethyl)amino]butoxy]phenyl]acetic acid which exhibit improved physical properties and stability. The invention also relates to pharmaceutical compositions including an effective amount of the metal salts, as well as methods of treating cancer including administration of a pharmaceutical composition including a salt of the invention to a subject in need thereof.

10 Claims, 11 Drawing Sheets

(56) References Cited

U.S. PATENT DOCUMENTS

| | | |
|---|---|---|
| 8,357,679 B2 | 1/2013 | Cooke et al. |
| 8,993,628 B2 | 3/2015 | Forman et al. |
| 9,399,028 B2 | 7/2016 | Tavazoie et al. |
| 9,421,218 B2 | 8/2016 | Hernando et al. |
| 9,526,710 B2 | 12/2016 | Tavazoie et al. |
| 9,707,195 B2 | 7/2017 | Tavazoie et al. |
| 9,827,217 B2 | 11/2017 | Martinez et al. |
| 9,884,813 B1 | 2/2018 | Martinez et al. |
| 9,962,348 B2 | 5/2018 | Tavazoie et al. |
| 10,543,183 B2 | 1/2020 | Tavazoie et al. |
| 10,669,296 B2 | 6/2020 | Martinez et al. |
| 10,869,926 B2 | 12/2020 | Zhou et al. |
| 10,945,978 B2 | 3/2021 | Tavazoie et al. |
| 11,174,220 B2 | 11/2021 | Wald et al. |
| 11,214,536 B2 | 1/2022 | Chitre et al. |
| 11,459,292 B2 | 10/2022 | Wald et al. |
| 2002/0022018 A1 | 2/2002 | Curiel et al. |
| 2002/0107233 A1 | 8/2002 | Liao et al. |
| 2003/0022375 A1 | 1/2003 | Itoh et al. |
| 2003/0027335 A1 | 2/2003 | Ruley et al. |
| 2003/0125357 A1 | 7/2003 | Adams et al. |
| 2003/0153541 A1 | 8/2003 | Dudley et al. |
| 2004/0072868 A1 | 4/2004 | Collins et al. |
| 2004/0087632 A1 | 5/2004 | Van Camp et al. |
| 2004/0216178 A1 | 10/2004 | Jones et al. |
| 2005/0080111 A1 | 4/2005 | Bayne et al. |
| 2005/0107444 A1 | 5/2005 | Thompsom et al. |
| 2005/0113419 A1 | 5/2005 | Huang et al. |
| 2005/0113580 A1 | 5/2005 | Thompson et al. |
| 2005/0130919 A1 | 6/2005 | Xu et al. |
| 2005/0131014 A1 | 6/2005 | Collini et al. |
| 2005/0215577 A1 | 9/2005 | Dehmlow et al. |
| 2005/0245515 A1 | 11/2005 | Dehmlow et al. |
| 2005/0261319 A1 | 11/2005 | Deuschle et al. |
| 2005/0282908 A1 | 12/2005 | Collins et al. |
| 2005/0289659 A1 | 12/2005 | Jacks et al. |
| 2006/0030612 A1 | 2/2006 | Steffan et al. |
| 2006/0074115 A1 | 4/2006 | Dehmlow et al. |
| 2006/0135601 A1 | 6/2006 | Dehmlow et al. |
| 2006/0160079 A1 | 7/2006 | Lane |
| 2006/0178398 A1 | 8/2006 | Adams et al. |
| 2007/0093524 A1 | 4/2007 | Nambi et al. |
| 2007/0161553 A1 | 7/2007 | Mathieu et al. |
| 2008/0085879 A1 | 4/2008 | Xie et al. |
| 2009/0004297 A1 | 1/2009 | Ranganathan |
| 2009/0030082 A1 | 1/2009 | Forman |
| 2009/0099066 A1 | 4/2009 | Moulton et al. |
| 2009/0175791 A1 | 7/2009 | Kavile et al. |
| 2009/0247587 A1 | 10/2009 | Okuda et al. |
| 2009/0286780 A1 | 11/2009 | Okuda et al. |
| 2010/0048944 A1 | 2/2010 | Parhami |
| 2010/0056481 A1 | 3/2010 | Glausch et al. |
| 2010/0069367 A1 | 3/2010 | Boren et al. |
| 2010/0249096 A1 | 9/2010 | Aay et al. |
| 2010/0273816 A1 | 10/2010 | Bernotas et al. |
| 2010/0279918 A1 | 11/2010 | Langel et al. |
| 2010/0284990 A1 | 11/2010 | Kaemmerer et al. |
| 2010/0298410 A1 | 11/2010 | Obad et al. |
| 2011/0028384 A1 | 2/2011 | Blacklow et al. |
| 2011/0112135 A1 | 5/2011 | Singhaus, Jr. et al. |
| 2011/0166079 A1 | 7/2011 | Vitek et al. |
| 2011/0237791 A1 | 9/2011 | Kawaguchi et al. |
| 2012/0156216 A1 | 6/2012 | Oh |
| 2012/0156263 A1 | 6/2012 | Choy et al. |
| 2012/0231457 A1 | 9/2012 | Tezapsidis et al. |
| 2013/0004481 A1 | 1/2013 | Solca et al. |
| 2013/0071403 A1 | 3/2013 | Rolland et al. |
| 2014/0186295 A1 | 7/2014 | Kupper et al. |
| 2015/0023955 A1 | 1/2015 | Tavazoie et al. |
| 2015/0033693 A1 | 2/2015 | Ito et al. |
| 2015/0045399 A1 | 2/2015 | Mohan |
| 2015/0051214 A1 | 2/2015 | Dong et al. |
| 2015/0065515 A1 | 3/2015 | Dong et al. |
| 2015/0073053 A1 | 3/2015 | Tavazoie et al. |
| 2015/0080406 A1 | 3/2015 | Leftheris et al. |
| 2015/0150941 A1 | 6/2015 | Weinberg et al. |
| 2015/0152094 A1 | 6/2015 | Mohan |
| 2015/0225366 A1 | 8/2015 | Li |
| 2015/0246924 A1 | 9/2015 | Dong et al. |
| 2015/0299136 A1 | 10/2015 | Busch et al. |
| 2016/0271149 A1 | 9/2016 | Einhorn |
| 2017/0066791 A1 | 3/2017 | Martinez et al. |
| 2017/0119807 A1 | 5/2017 | Lee et al. |
| 2018/0072810 A1 | 3/2018 | Afar et al. |
| 2019/0029984 A1 | 1/2019 | Tavazoie et al. |
| 2019/0125745 A1 | 5/2019 | Martinez et al. |
| 2021/0220306 A1 | 7/2021 | Tavazoie et al. |
| 2022/0127680 A1 | 4/2022 | Tavazoie et al. |

FOREIGN PATENT DOCUMENTS

| | | |
|---|---|---|
| AU | 2003226094 A1 | 10/2003 |
| AU | 2005272043 B2 | 2/2006 |
| AU | 2006227435 A1 | 9/2006 |
| CA | 2592367 C | 4/2011 |
| CN | 101952293 A | 1/2011 |
| CN | 103054844 B | 4/2014 |
| CN | 104780976 A | 7/2015 |
| CN | 108738323 A | 11/2018 |
| CN | 109251974 A | 1/2019 |
| DE | 2951400 A1 | 7/1981 |
| EP | 0015505 B1 | 8/1984 |
| EP | 0519596 A1 | 12/1992 |
| EP | 0592106 A1 | 4/1994 |
| EP | 0747053 A2 | 12/1996 |
| EP | 0735144 B1 | 6/2002 |
| EP | 2235019 A1 | 10/2010 |
| EP | 2474617 A1 | 7/2012 |
| EP | 2188266 B1 | 10/2012 |
| EP | 2584045 A1 | 4/2013 |
| ES | 2233700 T3 | 6/2005 |
| ES | 2525217 T3 | 12/2014 |
| ES | 2694726 T3 | 12/2018 |
| FR | 2865736 B1 | 7/2006 |
| GB | 946902 A | 1/1964 |
| JP | H11-507371 A | 6/1999 |
| JP | 2003-33179 A | 2/2003 |
| JP | 2006-232703 A | 9/2006 |
| JP | 2008-509948 A | 4/2008 |
| JP | 2008-526841 A | 7/2008 |
| JP | 2008-179562 A | 8/2008 |
| JP | 2011-525616 A | 9/2011 |
| JP | 2012-503984 A | 2/2012 |
| JP | 2012-528180 A | 11/2012 |
| JP | 5399262 B2 | 1/2014 |
| JP | 5511079 B2 | 6/2014 |
| JP | 2015-532642 A | 11/2015 |
| JP | 5851400 B2 | 2/2016 |
| KR | 10-2007-0116060 A | 12/2007 |
| KR | 10-2010-0102110 A | 9/2010 |
| MX | 2010012579 A | 12/2010 |
| RU | 2383524 C2 | 3/2010 |
| TW | 200606157 A | 2/2006 |
| TW | 200825054 A | 6/2008 |
| TW | 200922582 A | 6/2009 |
| WO | WO-95/16791 A1 | 6/1995 |
| WO | WO-96/39135 A1 | 12/1996 |
| WO | WO-00/66611 A1 | 11/2000 |
| WO | WO-01/66534 A2 | 9/2001 |
| WO | WO-02/13594 A1 | 2/2002 |
| WO | WO-02/24632 A2 | 3/2002 |
| WO | WO-02/090375 A2 | 11/2002 |
| WO | WO-03/031408 A2 | 4/2003 |
| WO | WO-03/043998 A1 | 5/2003 |
| WO | WO-03/045382 A1 | 6/2003 |
| WO | WO-03/059874 A2 | 7/2003 |
| WO | WO-03/059884 A1 | 7/2003 |
| WO | WO-03/060078 A2 | 7/2003 |
| WO | WO-03/082198 A2 | 10/2003 |
| WO | WO-03/082205 A2 | 10/2003 |
| WO | WO-03/082802 A1 | 10/2003 |
| WO | WO-03/090732 A1 | 11/2003 |
| WO | WO-03/090746 A1 | 11/2003 |
| WO | WO-03/090869 A1 | 11/2003 |

(56) References Cited

FOREIGN PATENT DOCUMENTS

| | | |
|---|---|---|
| WO | WO-03/099769 A1 | 12/2003 |
| WO | WO-03/099775 A1 | 12/2003 |
| WO | WO-03/106435 A1 | 12/2003 |
| WO | WO-2004/009091 A1 | 1/2004 |
| WO | WO-2004/011448 A1 | 2/2004 |
| WO | WO-2004/026816 A1 | 4/2004 |
| WO | WO-2004/043939 A1 | 5/2004 |
| WO | WO-2004/058717 A1 | 7/2004 |
| WO | WO-2004/072041 A1 | 8/2004 |
| WO | WO-2004/072042 A2 | 8/2004 |
| WO | WO-2004/072046 A2 | 8/2004 |
| WO | WO-2004/078939 A2 | 9/2004 |
| WO | WO-2005/005416 A1 | 1/2005 |
| WO | WO-2005/005417 A1 | 1/2005 |
| WO | WO-2005/016277 A2 | 2/2005 |
| WO | WO-2005/023782 A1 | 3/2005 |
| WO | WO-2005/039643 A2 | 5/2005 |
| WO | WO-2005/058834 A2 | 6/2005 |
| WO | WO-2005/077122 A2 | 8/2005 |
| WO | WO-2005/077124 A2 | 8/2005 |
| WO | WO-2005/112620 A2 | 12/2005 |
| WO | WO-2005/113499 A1 | 12/2005 |
| WO | WO-2006/000323 A1 | 1/2006 |
| WO | WO-2006/003923 A1 | 1/2006 |
| WO | WO-2006/004030 A1 | 1/2006 |
| WO | WO-2006/017055 A2 | 2/2006 |
| WO | WO-2006/018182 A1 | 2/2006 |
| WO | WO-2006/046593 A1 | 5/2006 |
| WO | WO-2006/073363 A1 | 7/2006 |
| WO | WO-2006/073364 A1 | 7/2006 |
| WO | WO-2006/073365 A1 | 7/2006 |
| WO | WO-2006/073366 A1 | 7/2006 |
| WO | WO-2006/073367 A1 | 7/2006 |
| WO | WO-2006/094034 A1 | 9/2006 |
| WO | WO-2006/102067 A1 | 9/2006 |
| WO | WO-2006/109633 A1 | 10/2006 |
| WO | WO-2007/002563 A1 | 1/2007 |
| WO | WO-2007/022563 A1 | 3/2007 |
| WO | WO-2007/047991 A1 | 4/2007 |
| WO | WO-2007/050425 A2 | 5/2007 |
| WO | WO-2007/081335 A1 | 7/2007 |
| WO | WO-2007/092065 A2 | 8/2007 |
| WO | WO-2008/011071 A2 | 1/2008 |
| WO | WO-2008/027988 A2 | 3/2008 |
| WO | WO-2008/049047 A2 | 4/2008 |
| WO | WO-2008/065754 A1 | 6/2008 |
| WO | WO-2009/020683 A2 | 2/2009 |
| WO | WO-2009/021868 A2 | 2/2009 |
| WO | WO-2009/024550 A1 | 2/2009 |
| WO | WO-2009/040289 A1 | 4/2009 |
| WO | WO-2009/043353 A2 | 4/2009 |
| WO | WO-2009/074467 A1 | 6/2009 |
| WO | WO-2009/086123 A1 | 7/2009 |
| WO | WO-2009/086129 A1 | 7/2009 |
| WO | WO-2009/086130 A1 | 7/2009 |
| WO | WO-2009/086138 A1 | 7/2009 |
| WO | WO-2009/133692 A1 | 11/2009 |
| WO | WO-2009/138438 A1 | 11/2009 |
| WO | WO-2009/144961 A1 | 12/2009 |
| WO | WO-2009/148915 A2 | 12/2009 |
| WO | WO-2009/150109 A1 | 12/2009 |
| WO | WO-2010/023317 A1 | 3/2010 |
| WO | WO-2010/025169 A2 | 3/2010 |
| WO | WO-2010/025179 A1 | 3/2010 |
| WO | WO-2010/036613 A1 | 4/2010 |
| WO | WO-2010/036959 A2 | 4/2010 |
| WO | WO-2010/059627 A1 | 5/2010 |
| WO | WO-2010/125811 A1 | 11/2010 |
| WO | WO-2010/138598 A2 | 12/2010 |
| WO | WO-2011/014661 A2 | 2/2011 |
| WO | WO-2011/051282 A1 | 5/2011 |
| WO | WO-2011/055391 A1 | 5/2011 |
| WO | WO-2011/103175 A2 | 8/2011 |
| WO | WO-2011/115892 A1 | 9/2011 |
| WO | WO-2011/130426 A2 | 10/2011 |
| WO | WO-2011/158667 A1 | 12/2011 |
| WO | WO-2012/004748 A1 | 1/2012 |
| WO | WO-2012/095505 A1 | 7/2012 |
| WO | WO-2012/096573 A1 | 7/2012 |
| WO | WO-2012/135082 A1 | 10/2012 |
| WO | WO-2013/043569 A1 | 3/2013 |
| WO | WO-2013/057148 A1 | 4/2013 |
| WO | WO-2013/076257 A1 | 5/2013 |
| WO | WO-2013/130892 A1 | 9/2013 |
| WO | WO-2013/138565 A1 | 9/2013 |
| WO | WO-2013/138568 A1 | 9/2013 |
| WO | WO-2014/028461 A2 | 2/2014 |
| WO | WO-2014/144037 A1 | 9/2014 |
| WO | WO-2015/065505 A1 | 5/2015 |
| WO | WO-2015/106164 A1 | 7/2015 |
| WO | WO-2016/100619 A2 | 6/2016 |
| WO | WO-2017/123568 A2 | 7/2017 |
| WO | WO-2017/161188 A1 | 9/2017 |
| WO | WO-2017/181163 A2 | 10/2017 |
| WO | WO-2018/161054 A1 | 9/2018 |
| WO | WO-2019/104062 A1 | 5/2019 |
| WO | WO-2020/176846 A2 | 9/2020 |
| WO | WO-2020/205644 A1 | 10/2020 |
| WO | WO-2021/119397 A1 | 6/2021 |

OTHER PUBLICATIONS

Bartel, "MicroRNAs: Target Recognition and Regulatory Functions," Cell. 136(2): 215-233 (2009).

Bastin et al., "Salt selection and optimisation procedures for pharmaceutical new chemical entities," Org Process Res Dev 4(5):427-35 (2000).

Benn et al., "Low-density lipoprotein cholesterol and the risk of cancer: a mendelian randomization study," J Natl Cancer Inst. 103(6):508-19 (Mar. 16, 2011).

Berge et al., "Pharmaceutical salts," J Pharm Sci. 66(1):1-19 (1977).

Bergenfelz et al., "Systemic Monocytic-MDSCs Are Generated from Monocytes and Correlate with Disease Progression in Breast Cancer Patients," PLOS One. 10(5):e0127028 (2015) (23 pages).

Bird et al., "Single-chain antigen-binding proteins," Science. 242(4877):423-6 (1988) (5 pages).

Bobin-Dubigeon et al., "Liver X Receptor (LXR)-regulated Genes of Cholesterol Trafficking and Breast Cancer Severity," Anticancer Res. 37(10):5495-5498 (2017).

Bordwell et al., "Synthesis of aryl methyl sulfoxides and determination of the conjugative effect of the methylsulfinyl group," J Am Chem Soc. 79(3): 717-22 (1957).

Brunton et al., "Goodman and Gilman's the Pharmacological Basis of Therapeutics," McGraw Hill Companies (2011).

Bustin, "Absolute quantification of mRNA using real-time reverse transcription polymerase chain reaction assays," Journal of Molecular Endocrinology. 25(2): 169-193 (2000).

Caira, "Crystalline polymorphism of organic compounds," *Topics in Current Chemistry*, vol. 198. Springer Verlag Berlin Heidelberg, 163-208 (1998).

Calin et al., "MicroRNA signatures in human cancers," Nat Rev Cancer. 6:857-866 (2007).

CAPLUS AN 1981:121135 for Ostermayer et al., "3-Amino-1, 2-propane diol derivatives and pharmaceutical compositions containing them," (1981) (2 pages).

CAPLUS AN 1981:586827 for Mohr, R., "N, N'-Diarylethylendiamines or N, N', N"-triaryldiethylenetriamines," (1981) (1 page).

CAPLUS AN 1983:178855 for Fujikura et al., "Studies on benzenesulfonamide derivatives with α- and β-adrenergic antagonistic and antihypertensive activities," Chemical & Pharmaceutical Bulletin 30(11):4092-101 (1982).

CAPLUS AN 2002:240713 for Collins et al., "Preparation of substituted phenylacetamides and benzamides as agonists for Liver X receptors (LXR)," (2002) (2 pages).

CAPLUS AN 2003:796421 for Cairns et al., "Methods of treatment with LXR modulators," (2003).

CAPLUS AN 2003:796645 for Thompson et al., "Preparation of (hetero)arylalkanoic acids and esters as LXR agonists," (2003) (2 pages).

(56) References Cited

OTHER PUBLICATIONS

CAPLUS, AN 2005:238962, for Yamazaki et al., "Preparation of azole compounds as PPAR-alpha agonists," (2005) (4 pages).
CAPLUS, AN 2006:910678, for Yamaguchi et al., "Preparation of phenoxyacetic acid compounds containing furan moiety as peroxisome proliferator activation receptor (PPAR) alpha/gamma agonists," (2006) (2 pages).
Carell et al., "A Solution-Phase Screening Procedure for the Isolation of Active Compounds from a Library of Molecules," Angewandte Chemie International Edition in English. 33(20): 2061-2064 (1994).
Chang et al., "Apolipoprotein E4 allele influences the response of plasma triglyceride levels to tamoxifen in breast cancer patients," Clin Chim Acta. 401(1-2):144-7 (Mar. 2009).
Chinese Office Action dated Aug. 30, 2021 in related Chinese Application No. 2018115020665 (20 pages).
Cho et al., "An unnatural biopolymer," Science. 261(5126):1303-1305 (1993).
Chuu et al., "Antiproliferative effect of LXR agonists T0901317 and 22(R)-hydroxycholesterol on multiple human cancer cell lines," Anticancer Res. 30(9):3643-8 (2010).
Chuu et al., "Modulation of liver X receptor signaling as novel therapy for prostate cancer," J Biomed Sci. 14(5):543-553 (2007).
Communication pursuant to Article 94(3) EPC for European Application No. 13829165.3, dated Jan. 15, 2018 (5 pages).
Communication pursuant to Article 94(3) EPC for European Application No. 15734952.3, dated Jul. 18, 2019 (6 pages).
Communication pursuant to Article 94(3) EPC for European Patent Application No. 15734952.3, dated Aug. 29, 2018 (6 pages).
Cristiano et al., "Molecular conjugates: a targeted gene delivery vector for molecular medicine," J Mol Med. 73:479-486 (1995).
Cull et al., "Screening for receptor ligands using large libraries of peptides linked to the C terminus of the lac repressor," Proc Natl Acad Sci. 89(5):1865-1869. (1992).
Cwirla et al., "Peptides on phage: A vast library of peptides for identifying ligands," Proc Nati Acad Sci. 87:6378-6382 (1990).
Devlin et al., "Random peptide libraries: a source of specific protein binding molecules," Science. 249(4967):404-406 (1990).
DeWitt et al., "'Diversomers': an approach to nonpeptide, nonoligomeric chemical diversity," Proc Natl Acad Sci. 90(15):6909-6913 (1993).
Domingues et al., "Immunotherapy and lung cancer: current developments and novel targeted therapies," Immunotherapy. 6(11):1221-35 (Dec. 12, 2014) (Abstract only).
Draghiciu et al., "Myeloid derived suppressor cells—An overview of combat strategies to increase immunotherapy efficacy," Oncoimmunology. 4(1):e954829 (Feb. 3, 2015) (10 pages).
Erb et al., "Recursive deconvolution of combinatorial chemical libraries," Proc Natl Acad Sci. 91(24):11422-11426 (1994).
Examination Report No. 1 for Australian Patent Application No. 2013302861, dated Sep. 8, 2017 (6 pages).
Extended European Search Report for European Application No. 13829165.3, dated Jun. 8, 2016 (12 pages).
Extended European Search Report for European Application No. 18880192.2, dated Jul. 23, 2021 (9 pages).
Extended European Search Report for European Patent Application No. 15734952.3, dated Jul. 6, 2017 (8 pages).
Fabian et al., "Regulation of mRNA Translation and Stability by microRNAs," Annu Rev Biochem. 79:351-379 (2010) (32 pages).
Felici et al., "Selection of Antibody Ligands from a Large Library of Oligopeptides Expressed on a Multivalent Exposition Vector," J Mol Biol. 222:301-310 (1991).
Filipowicz et al., "Mechanisms of post-transcriptional regulation by microRNAs: are the answers in sight?," Nat Rev Genet. 9:102-114 (2008).
First Examination Report for Australian Application No. 2015204572, dated Jul. 15, 2019 (7 pages).
First Office Action and Search Report for Chinese Application No. 2013800534784, dated Aug. 1, 2017 (19 pages).
Fodor et al., "Multiplexed biochemical assays with biological chips," Nature. 364: 555-556 (1993).
Fowler et al., "Liver X receptor activators display anti-inflammatory activity in irritant and allergic contact dermatitis models: liver-X-receptor-specific inhibition of inflammation and primary cytokine production," J Invest Dermatol. 120(2):246-55 (2003).
Gallop et al., "Applications of Combinatorial Technologies to Drug Discovery. 1. Background and Peptide Combinatorial Libraries," J Med Chem 37(9):1233-51 (1994).
Garbe et al., "Melanoma epidemiology and trends," Clinics in Dermatology. 27(1): 3-9 (2009).
Garbe et al., "Systematic review of medical treatment in melanoma: current status and future prospects," Oncologist. 16(1):5-24 (2011).
Gielen et al., "Increase in Both CD14-Positive and CD15-Positive Myeloid-Derived Suppressor Cell Subpopulations in the Blood of Patients With Glioma But Predominance of CD15-Positive Myeloid-Derived Suppressor Cells in Glioma Tissue," J Neuropathol Exp Neur. 74(5):390-400 (2015).
Ginzinger, "Gene quantification using real-time quantitative PCR: An emerging technology hits the mainstream," Exp Hematol. 30(6): 503-512 (2002).
Groot et al., "Synthetic LXR agonists increase LDL in CETP species," J Lipid Res. 46(10):2182-91 (2005).
Gros et al., "Myeloid Cells Obtained from the Blood but Not from the Tumor can Suppress T-cell Proliferation in Patients with Melanoma," Clin Cancer Res. 18(19):5212-5223 (2012).
Guo et al., "Mammalian microRNAs predominantly act to decrease target mRNA levels," Nature. 466:835-840 (2010).
Guo et al., "Research Progress in Apolipoprotein E in Thrombosis—related Diseases and Malignant Tumors," Chinese General Practice. 16(2B):590-2 (2013). English abstract included.
Gupta et al., "Cancer Metastasis: Building a Framework," Cell. 127(4):679-695 (2006).
Gupta et al., "Long non-coding RNA HOTAIR reprograms chromatin state to promote cancer metastasis," Nature. 464:1071-1076 (2010) (8 pages).
Guttman et al., "Chromatin signature reveals over a thousand highly conserved large non-coding RNAs in mammals," Nature. 458:223-227 (2009).
Haas, "Melanoma: three ways around BRAF inhibition," SciBX. 3(47):(2010) (3 pages).
Hanahan et al., "Hallmarks of Cancer: The Next Generation," Cell. 144(5):646-674 (2011).
Haqq et al., "The gene expression signatures of melanoma progression," Proc Natl Acad Sci USA. 102(17):6092-6097 (2005).
Hatters et al., "Apolipoprotein E structure: insights into function," Trends in Biochemical Sciences. 31(8):445-454 (2006).
Hatziapostolou et al., "An HNF4alpha-miRNA Inflammatory Feedback Circuit Regulates Hepatocellular Oncogenesis," Cell. 147(6):1233-1247 (2011).
Hauser et al., "Apolipoprotein E: From lipid transport to neurobiology," Progress in Lipid Research. 50(1):62-74 (2001).
Huang et al., "The microRNAs miR-373 and miR-520c promote tumour invasion and metastasis," Nat Cell Biol. 10(2):202-210 (2008) (24 pages).
Huarte et al., "A Large Intergenic Noncoding RNA Induced by p53 Mediates Global Gene Repression in the p53 Response," Cell. 142(3):409-419 (2010).
Hurst et al., "Metastamir: The Field of Metastasis-Regulatory microRNA Is Spreading," Cancer Res. 69(19):7495-7498 (2009).
Huston et al., "Protein engineering of antibody binding sites: recovery of specific activity in an anti-digoxin single-chain Fv analogue produced in *Escherichia coli*.," Proceedings of the National Academy of Sciences. 85(16):5879-5883 (1988).
Hynes et al., "Metastatic Potential: generic predisposition of the primary tumor or rare, metastatic variants-or both?" Cell. 113(7):821-823 (2003).
Inglis et al., "Synthesis and evaluation of 3-(Dihydroxyboryl)benzoic acids as D,D-Carboxypeptidase R39 inhibitors," J Med Chem. 52(19):6097-106 (2009).
International Search Report and Written Opinion for International Application No. PCT/US15/66289, dated Feb. 25, 2016 (14 pages).
International Search Report and Written Opinion for International Application No. PCT/US17/12906, dated Jun. 30, 2017 (14 pages).

(56) References Cited

OTHER PUBLICATIONS

International Search Report and Written Opinion for International Application No. PCT/US18/62063, dated Feb. 4, 2019 (20 pages).
International Search Report and Written Opinion for International Application No. PCT/US20/50075, dated Feb. 10, 2021 (16 pages).
International Search Report and Written Opinion for International Application No. PCT/US20/64456, dated Mar. 3, 2021 (13 pages).
International Search Report and Written Opinion for International Patent Application No. PCT/US2015/010909, dated Jun. 11, 2015 (14 pages).
International Search Report for International Application No. PCT/US13/54690, dated Feb. 21, 2014 (10 pages).
International Search Report for International Application No. PCT/US20/20349, dated Oct. 29, 2020 (8 pages).
Invitation to Pay Additional Fees for International Application No. PCT/US2015/010909, dated Mar. 11, 2015 (3 pages).
Jemal et al., "Cancer Statistics, 2008," CA Cancer J Clin. 58(2):71-96 (2008).
Johnson et al., "Relationships between drug activity in NCI preclinical in vitro and in vivo models and early clinical trials," Br J Cancer. 84(10):1424-31 (2001).
Ju et al., "Liver X receptors as potential targets for cancer therapeutics," Oncol Lett. 14(6):7676-80 (2017).
Kang et al., "A multigenic program mediating breast cancer metastasis to bone," Cancer Cell. 3(6):537-549 (2003).
Kitano et al., "Computational algorithm-driven evaluation of monocytic myeloid-derived suppressor cell frequency for prediction of clinical outcomes," Cancer Immunol Res. 2(8):812-821 (2014) (11 pages).
Lam et al., "A new type of synthetic peptide library for identifying ligand-binding activity," Nature. 354(6348):82-84 (1991).
Li et al., "Liver X receptor modulators: a review of recently patented compounds (2007-2009)," Expert Opin Ther Pat. 20(4):535-62 (2010).
Li et al., "miR-495 and miR-551a inhibit the migration and invasion of human gastric cancer cells by directly interacting with PRL-3," Cancer Lett. 323(1):41-47 (2012).
Loewer et al., "Large intergenic non-coding RNA-RoR modulates reprogramming of human induced pluripotent stem cells," Nat Genet. 42(12):1113-1117 (2010) (8 pages).
Lucas et al., "Solar ultraviolet radiation: Global burden of disease from solar ultraviolet radiation," Environmental Burden of Disease Series. 13 (2006) (95 pages).
Lujambio et al., "The microcosmos of cancer," Nature. 482(7385):347-355 (2012).
Ma et al., "Tumour invasion and metastasis initiated by microRNA-10b in breast cancer," Nature. 449(7163):682-688 (2007) (9 pages).
Marino et al., "The discovery of tertiary-amine LXR agonists with potent cholesterol efflux activity in macrophages," Bioorg Med Chem Lett. 19(19):5617-21 (2009).
Minn et al., "Genes that mediate breast cancer metastasis to lung," Nature. 436(7050):518-524 (2005).
Morissette et al., "High-throughput crystallization: polymorphs, salts, co-crystals and solvates of pharmaceutical solids," Adv Drug Deliv Rev. 56(3):275-300 (2004).
Obermajer et al., "$PGE_2$-Induced CXCL12 Production and CXCR4 Expression Controls the Accumulation of Human MDSCs in Ovarian Cancer Environment," Cancer Res. 71(24):7463-7470 (2011) (9 pages).
Office Action for Japanese Application No. 2015-527533, dated Jun. 6, 2017 (13 pages).
Office Action for Japanese Application No. 2015-527533, dated Nov. 14, 2017 (5 pages).
Olson et al., "MicroRNA dynamics in the stages of tumorigenesis correlate with hallmark capabilities of cancer," Genes Dev. 23(18):2152-2165 (2009) (15 pages).
Ong et al., "Quantitative Real-time PCR: A Critique of Method and Practical Considerations," Hematology. 7(1):59-67 (2002) (10 pages).
Ostrand-Rosenberg et al., "Myeloid-derived suppressor cells: linking inflammation and cancer," J Immunol. 182(8):4499-4506 (2009).

Padlan, "A possible procedure for reducing the immunogenicity of antibody variable domains while preserving their ligand-binding properties," Mol Immunol. 28(4-5):489-498 (1991).
Partial Supplementary European Search Report for European Patent Application No. 20763347.0, dated Nov. 4, 2022 (25 pages).
Pencheva et al., "Broad-Spectrum therapeutic suppression of metastatic melanoma through nuclear hormone receptor activation," Cell. 156(5):986-1001 (2014).
Pencheva et al., "Control of Metastatic Progression by microRNA Regulatory Networks," Available in PMC Dec. 15, 2015, published in final edited form as: Nat Cell Biol. 15(6):546-554 (2013) (21 pages).
Pencheva et al., "Convergent multi-miRNA targeting of ApoE drives LRP1/LRP8-dependent melanoma metastasis and angiogenesis," available in PMC Nov. 21, 2013, published in final edited form as: Cell. 151(5):1068-82 (2012) (27 pages).
Png et al., "A microRNA regulon that mediates endothelial recruitment and metastasis by cancer cells," Nature. 481(7380):190-194 (2012) (7 pages).
Poliseno et al., "A coding-independent function of gene and pseudogene mRNAs regulates tumour biology," Nature. 465(7301):1033-1038 (2010) (8 pages).
Pollack et al., "Use of Young Nude Mice for Selection of Subpopulations of Cells With Increased Metastatic Potential From Nonsyngeneic Neoplasms," J Natl Cancer Inst. 69(1):137-141 (1982).
Ponomarev et al., "A novel triple-modality reporter gene for whole-body fluorescent, bioluminescent, and nuclear noninvasive imaging," Eur J Nucl Med Mol Imaging. 31(5):740-751 (2004).
PubChem Compound Summary for CID 10301050, created Oct. 25, 2006, modified Jan. 19, 2019 (9 pages).
PubChem Compound Summary for CID 422253, created Mar. 26, 2005, modified Jan. 19, 2019 (11 pages).
PubChem Compound Summary for CID 68861577, created Nov. 30, 2012, modified Oct. 24, 2020 (10 pages).
PubChem Substance Record for SID 168474198, available Dec. 2, 2013 (6 pages).
PubChem. Compound Summary for CID 51369, created Mar. 27, 2005, <https://pubchem.ncbi.nlm.nih.gov/compound/51369?from=summary>, retrieved on Feb. 23, 2015 (18 pages).
PubChem. Compound Summary for CID 52723103, created May 20, 2011 <https://pubchem.ncbi.nlm.nih.gov/compound/52723103>, retrieved on Nov. 7, 2016 (10 pages).
Riddell et al. "The LXR agonist TO901317 selectively lowers hippocampal Abeta42 and improves memory in the Tg2576 mouse model of Alzheimer's disease," Mol Cell Neurosci. 34(4):621-8 (2007).
Riechmann et al., "Reshaping human antibodies for therapy," Nature. 332(6162): 323-327 (1988).
Roguska et al., "Humanization of murine monoclonal antibodies through variable domain resurfacing," Proc Nat Acad Sci U S A. 91(3):969-973 (1994).
Rough et al., "Anti-proliferative effect of LXR agonist T0901317 in ovarian carcinoma cells," J Ovarian Res. 3:13 (2010) (10 pages).
Roz et al., "Macrophage apolipoprotein E and proliferation of MCF-7 breast cancer cells: role of LXR," Anticancer Res. 33(9):3783-9 (2013).
Rudolph et al., "Increased frequencies of $CD11b^+CD33^+CD14^+$ HLA-$DR^{low}$ myeloid-derived suppressor cells are an early event in melanoma patients," Exp Dermatol. 23(3):202-204 (2014).
Sausville et al., "Contributions of human tumor xenografts to anticancer drug development," Cancer Res. 66(7):3351-4 (2006).
Schmuth et al. "Thematic review series: skin lipids. Peroxisome proliferator-activated receptors and liver X receptors in epidermal biology," J Lipid Res. 49(3):499-509 (2008).
Scoles et al., "Liver X receptor agonist inhibits proliferation of ovarian carcinoma cells stimulated by oxidized low density lipoprotein," Gynecol Oncol. 116(1):109-116 (2010).
Scott et al., "Searching for peptide ligands with an epitope library," Science. 249(4967):386-390 (1990).
Second Office Action for Chinese Application No. 201380053478.4, dated Mar. 13, 2018 (8 pages).

(56) References Cited

OTHER PUBLICATIONS

Speidell et al., "Development of a Human APOE Knock-in Mouse Model for Study of Cognitive Function After Cancer Chemotherapy," Neurotox Res. 35(2):291-303 (Feb. 2019).
Spencer et al., "Pharmacophore Analysis of the Nuclear Oxysterol Receptor LXRalpha," J Med Chem. 44(6):886-897 (2001).
Srivastava et al., "Targeting myeloid-derived suppressor cells augments antitumor activity against lung cancer," Immunotargets Ther. 2012(1):7-12 (Oct. 1, 2012).
Studnicka et al., "Human-engineered monoclonal antibodies retain full specific binding activity by preserving non-CDR complementarity-modulating residues," Protein Eng. 7(6):805-814 (1994).
Suon et al., "Systemic treatment with liver X receptor agonists raises apolipoprotein E, cholesterol, and amyloid-beta peptides in the cerebral spinal fluid of rats," Mol Neurodegener. 5:44 (2010) (14 pages).
Talmadge et al., "AACR Centennial Series: The Biology of Cancer Metastasis: Historical Perspective," Cancer Res. 70(14):5649-5669 (2010).
Talmadge et al., "History of myeloid derived suppressor cells (MDSCs) in the macro- and micro-environment of tumour-bearing hosts," Available in PMC Mar. 13, 2015, published in final edited form as: Nat Rev Cancer. 13(10):739-752 (2013) (34 pages).
Tavazoie et al., "Endogenous human microRNAs that suppress breast cancer metastasis," Nature. 451(7175):147-152 (2008) (8 pages).
Tavazoie et al., "LXR/ApoE Activation Restricts Innate Immune Suppression in Cancer," Article in Press, published in final edited form as: Cell. 172(4):825-40.e18 (2018) (35 pages).
Thaker, "In Situ RT-PCR and Hybridization Techniques," Methods Mol Biol. 115: 379-402 (1999).
Travis et al., "Facile oxidation of aldehydes to acids and esters with oxone," Org Lett. 5(7):1031-4 (2003).
Verghese et al., "ApoE influences amyloid-beta (Abeta) clearance despite minimal apoE/Abeta association in physiological conditions," Proc Natl Acad Sci U S A. 110(19):E1807-16 (May 7, 2013).
Viennois et al., "Selective liver X receptor modulators (SLIMs): What use in human health?" Mol Cell Endocrinol. 351(2):129-41 (2012).
Wang et al., "Gene-expression profiles to predict distant metastasis of lymph-node-negative primary breast cancer," Lancet. 365(9460):671-679 (2005).

Ward et al., "Binding activities of a repertoire of single immunoglobulin variable domains secreted from *Escherichia coli*," Nature. 341(6242):544-6 (1989).
Weber et al., "Phase I/II Study of Metastatic Melanoma Patients Treated with Nivolumab Who Had Progressed after Ipilimumab," Cancer Immunol Res. 4(4):345-53 (2016) (10 pages).
Wolchok et al., "Nivolumab plus ipilimumab in advanced melanoma," N Engl J Med. 369(2):122-33 (2013).
Written Opinion for International Application No. PCT/US13/54690, dated Feb. 21, 2014 (17 pages).
Yang et al., "Causal relevance of circulating high-density lipoprotein cholesterol with cancer: a Mendelian randomization meta-analysis," Sci Rep. 5:9495 (Mar. 30, 2015) (7 pages).
Zeng et al., "Liver X receptors agonists impede hepatitis C virus infection in an Idol-dependent manner," Antiviral Res. 95(3):245-56 (Sep. 2012).
Zhang et al., "A novel subset of B7-H3$^+$CD14$^+$HLA-DR$^{-/low}$ myeloid-derived suppressor cells are associated with progression of human NSCLC," Oncoimmunology. 4(2):e977164 (2015) (12 pages).
Zhang et al., "Liver X receptor activation induces apoptosis of melanoma cell through caspase pathway," Cancer Cell Int. 14(1):16 (2014) (6 pages).
Zhang et al., "The microRNA network and tumor metastasis," Oncogene. 29(7):937-948 (2010).
Zigler et al., "Tumor Immunotherapy in Melanoma: Strategies for Overcoming Mechanisms of Resistance and Escape," Am J Clin Dermatol. 9(5):307-313 (2008).
Zuckermann et al., "Discovery of Nanomolar Ligands for 7-Transmembrane G-Protein-Coupled Receptors from a Diverse N-(Substituted)glycine Peptoid Library," J Med Chem. 37(17):2678-2685 (1994).
Extended European Search Report for European Patent Application No. 20897654.8, dated Jun. 7, 2023 (5 Pages).
Fymat, "Harnessing the immune system to treat cancers and neurodegenerative diseases," Clinical Research in Neurology 1(1):1-14 (Apr. 4, 2018).
Simons et al., "T cell co-stimulation and co-inhibition in cardiovascular disease: a double-edged sword," Nat Rev Cardiol. 16(6):325-43 (Jun. 2019).
Tice et al., "The medicinal chemistry of liver X receptor (LXR) modulators," J Med Chem. 57(17):7182-205 (Sep. 11, 2014).
Zhang et al., "11ah Data Transmission Flow," PowerPoint slideshow dated Nov. 7, 2011, available <https://mentor.ieee.org/802.11/dcn/11/11-11-1484-00-00ah-11ah-phy-transmission-flow.pptx> (15 Pages).

* cited by examiner

METAL SALTS AND USES THEREOF

BACKGROUND

The Liver X Receptor (LXR) is a nuclear receptor transcription factor. It has been found that LXR modulators are useful in the treatment of a variety of diseases, including cancers. There is a need to provide salts of such compounds with improved stability and physical properties.

SUMMARY OF THE INVENTION

The invention provides a metal salt of an LXRβ agonist. The invention also provides a method of preparing such metal salts of the LXRβ agonist, pharmaceutical compositions including the metal salts, and methods of treating cancer with such compositions.

Accordingly, in an aspect, the invention features a metal salt (e.g., a pharmaceutically acceptable metal salt) of 2-[3-[(3R)-3-[[2-chloro-3-(trifluoromethyl)phenyl]methyl-(2,2-diphenylethyl)amino]butoxy]phenyl]acetic acid (Compound 1).

In some embodiments, the metal salt of 2-[3-[(3R)-3-[[2-chloro-3-(trifluoromethyl)phenyl]methyl-(2,2-diphenylethyl)amino]butoxy]phenyl]acetic acid is a multivalent metal salt.

In some embodiments, the metal salt of 2-[3-[(3R)-3-[[2-chloro-3-(trifluoromethyl)phenyl]methyl-(2,2-diphenylethyl)amino]butoxy]phenyl]acetic acid is a zinc salt, e.g., a 2:1 (Compound 1:zinc) salt.

In some embodiments, the metal salt of 2-[3-[(3R)-3-[[2-chloro-3-(trifluoromethyl)phenyl]methyl-(2,2-diphenylethyl)amino]butoxy]phenyl]acetic acid is an aluminum salt, e.g., a 3:1 (Compound 1:aluminum) salt.

In some embodiments, the metal salt of 2-[3-[(3R)-3-[[2-chloro-3-(trifluoromethyl)phenyl]methyl-(2,2-diphenylethyl)amino]butoxy]phenyl]acetic acid is a bismuth salt, e.g., a 3:1 (Compound 1:bismuth) salt.

In some embodiments, the metal salt of 2-[3-[(3R)-3-[[2-chloro-3-(trifluoromethyl)phenyl]methyl-(2,2-diphenylethyl)amino]butoxy]phenyl]acetic acid is a calcium salt, e.g., a 2:1 (Compound 1:calcium) salt.

In some embodiments, the metal salt is amorphous. In some embodiments, the metal salt (e.g., an amorphous zinc salt) has a peak with increased intensity relative to the free acid at about $1590\pm10$ cm$^{-1}$ and a peak with reduced intensity relative to the free acid at about $1710\pm10$ cm$^{-1}$ as measured by Fourier-transform infrared spectroscopy (FTIR). In some embodiments, the metal salt has less than 1% mass loss up to decomposition as measured by thermogravimetric analysis.

In another aspect, the invention features a method of producing a zinc salt (e.g., a 2:1 zinc salt) of Compound 1. This method includes combining Compound 1, or a salt thereof (e.g., a 1:1 sodium salt or the free compound), and a zinc salt (e.g., zinc chloride or zinc acetate) in an amount sufficient to produce the zinc salt of Compound 1.

In some embodiments of the method of producing a zinc salt, the method includes dissolving the Compound 1, or salt thereof, and the zinc salt in a solvent to form a mixture. In some embodiments, the solvent is water. In some embodiments, the solvent is a mixture of organic solvent (e.g., methanol) and water (e.g., 9:1 organic solvent and water by volume). In some embodiments of the method of producing a zinc salt, the method further includes cycling the temperature of the mixture between ambient temperature and 40° C.

In some embodiments of the method of producing a zinc salt, wherein said cycling is performed for 24 hours.

In another aspect, the invention features a pharmaceutically acceptable zinc salt of Compound 1 produced by any of the foregoing methods.

In another aspect, the invention features a method of producing an aluminum salt (e.g., a 3:1 aluminum salt) Compound 1. This method includes combining Compound 1, or a salt thereof (e.g., a 1:1 sodium salt or the free compound), and an aluminum salt (e.g., aluminum sulfate) in an amount sufficient to produce the aluminum salt of Compound 1.

In another aspect, the invention features a pharmaceutical composition containing any of the foregoing metal salts and a pharmaceutically acceptable excipient.

In some embodiments, the pharmaceutical composition includes less than 1.5 weight % of sodium. In some embodiments, the pharmaceutical composition is substantially free of the 1:1 sodium salt of Compound 1. In some embodiments, the pharmaceutical composition is in unit dosage form.

In another aspect, the invention features a method of treating cancer. This method includes administering an effective amount of any of the foregoing salts or pharmaceutical compositions.

In some embodiments of the method of treating cancer, the subject has a cancer that has failed to respond to a previously administered immunotherapy (e.g., the cancer of the subject has progressed despite treatment with the immunotherapy).

In some embodiments of the method of treating cancer, the cancer is resistant to an immunotherapy (e.g., the cancer has been determined to be resistant to immunotherapies such as by genetic markers or the level of MDSCs (e.g., monocytic and/or granulocytic MDSCs) in a sample, or is likely to be resistant, to immunotherapies such as a cancer that has failed to respond to an immunotherapy).

In another aspect, the invention features a method of treating cancer that has failed to respond to an immunotherapy in a subject. This method includes administering an effective amount of any of the foregoing salts or pharmaceutical compositions to the subject in combination with an immunotherapy.

In another aspect, the invention features a method of treating cancer that is resistant to immunotherapy in a subject. This method includes administering an effective amount of any of the foregoing salts or pharmaceutical compositions to the subject in combination with an immunotherapy.

In some embodiments of any of the methods of treating cancer, the cancer is breast cancer, colon cancer, renal cell cancer, lung cancer (e.g., non-small cell lung cancer), hepatocellular carcinoma, gastric cancer, ovarian cancer, pancreatic cancer, esophageal cancer, prostate cancer, sarcoma, glioblastoma, diffuse large B-cell lymphoma, leukemia, or melanoma. In some embodiments, the cancer is metastatic cancer. In some embodiments of any of the methods of treating cancer, the effective amount is an amount effective to suppress metastatic colonization of the cancer.

In certain embodiments of any of the methods of treating cancer, the cancer is a drug resistant cancer or has failed to respond to a prior therapy (e.g., a cancer resistant to, or a cancer that has failed to respond to prior treatment with, vemurafenib, dacarbazine, a CTLA-4 inhibitor, a PD-1 inhibitor, interferon therapy, a BRAF inhibitor, a MEK inhibitor, radiotherapy, temozolimide, irinotecan, a CAR-T therapy, herceptin, perjeta, tamoxifen, xeloda, docetaxol, platinum agents such as carboplatin, taxanes such as paclitaxel and docetaxel, ALK inhibitors, MET inihibitors, alimta, abraxane, adriamycin, gemcitabine, avastin, halaven, neratinib, a PARP inhibitor, brilanestrant, an mTOR inhibitor, topotecan, gemzar, a VEGFR2 inhibitor, a folate receptor antagonist, demcizumab, fosbretabulin, or a PDL-1 inhibitor).

In an embodiment of any of the methods of treating cancer, the immunotherapy, when present, is a CTLA-4 inhibitor, a PD-1 inhibitor, a PD-L1 inhibitor, or adoptive T-cell transfer therapy. In some embodiments, the immunotherapy includes a PD-1 inhibitor such as a PD-1 antibody, a PD-L1 inhibitor such as a PD-L1 antibody, a CTLA-4 inhibitor such as a CTLA-4 antibody, a CSF-1R inhibitor, an IDO inhibitor, an A1 adenosine inhibitor, an A2A adenosine inhibitor, an A2B adenosine inhibitor, an A3A adenosine inhibitor, an arginase inhibitor, or an HDAC inhibitor. In some embodiments, the immunotherapy includes a PD-1 inhibitor (e.g., nivolumab, pembrolizumab, pidilizumab, BMS 936559, and atezolizumab). In some embodiments, the immunotherapy includes a PD-L1 inhibitor (e.g., atezolizumab and durvalumab). In some embodiments, the immunotherapy includes a CTLA-4 inhibitor (e.g., ipilimumab). In some embodiments, the immunotherapy includes a CSF-1R inhibitor (e.g., pexidartinib and 4-(2,4-difluoroanilino)-7-ethoxy-6-(4-methylpiperazin-1-yl)quinoline-3-carboxamide). In some embodiments, the immunotherapy includes an IDO inhibitor (e.g., norharmane, rosmarinic acid, and alpha-methyl-tryptophan). In some embodiments, the immunotherapy includes an A1 adenosine inhibitor (e.g., 8-cyclopentyl-1,3-dimethylxanthine, 8-cyclopentyl-1,3-dipropylxanthine, 8-phenyl-1,3-dipropylxanthine, bamifylline, BG-9719, tonapofylline, FK-453, FK-838, rolofylline, or N-0861). In some embodiments, the immunotherapy includes an A2A adenosine inhibitor (e.g., ATL-4444, istradefylline, MSX-3, preladenant, SCH-58261, SCH-412348, SCH-442416, 2-butyl-9-methyl-8-(triazol-2-yl)purin-6-amine, VER-6623, VER-6947, VER-7835, viadenant, or ZM-241,385). In some embodiments, the immunotherapy includes an A2B adenosine inhibitor (e.g., N-[5-(1-cyclopropyl-2,6-dioxo-3-propyl-7H-purin-8-yl)pyridin-2-yl]-N-ethylpyridine-3-carboxamide, 3-ethyl-1-propyl-8-[1-[[3-(trifluoromethyl)phenyl]methyl]pyrazol-4-yl]-7H-purine-2,6-dione, MRS-1706, MRS-1754, N-[2-[[2-phenyl-6-[4-(3-phenylpropyl)piperazine-1-carbonyl]-7H-pyrrolo[2,3-d]pyrimidin-4-yl]amino]ethyl]acetamide, PSB-603, PSB-0788, or PSB-1115). In some embodiments, the immunotherapy includes an A3A adenosine inhibitor (e.g., KF-26777, MRS-545, MRS-1191, MRS-1220, MRS-1334, propyl 6-ethyl-5-ethylsulfanylcarbonyl-2-phenyl-4-propylpyridine-3-carboxylate, MRS-3777, MRE-3005-F20, MRE-3008-F20, PSB-11, OT-7999, VUF-5574, and SSR161421). In some embodiments, the immunotherapy includes an arginase inhibitor (e.g., an arginase antibody, (2s)-(+)-amino-5-iodoacetamidopentanoic acid, NG-hydroxy-L-arginine, (2S)-(+)-amino-6-iodoacetamidohexanoic acid, or (R)-2-amino-6-borono-2-(2-(piperidin-1-yl)ethyl)hexanoic acid. In some embodiments, the immunotherapy includes an HDAC inhibitor (e.g., valproic acid, SAHA, or romidepsin).

In another embodiment of any of the methods of treating cancer, the method further includes administering to the subject an additional anticancer therapy (e.g., an antiproliferative).

In particular embodiments, the antiproliferative is: a chemotherapeutic or cytotoxic agent, a differentiation-inducing agent (e.g., retinoic acid, vitamin D, cytokines), a hormonal agent, an immunological agent, or an anti-angiogenic agent. Chemotherapeutic and cytotoxic agents include, but are not limited to, alkylating agents, cytotoxic antibiotics, antimetabolites, vinca alkaloids, etoposides, and others (e.g., paclitaxel, taxol, docetaxel, taxotere, cis-platinum). A list of additional compounds having antiproliferative activity can be found in L. Brunton, B. Chabner and B. Knollman (eds). Goodman and Gilman's The Pharmacological Basis of Therapeutics, Twelfth Edition, 2011, McGraw Hill Companies, New York, NY.

In certain embodiments, the antiproliferative is a PD-1 inhibitor, a VEGF inhibitor, a VEGFR2 inhibitor, a PD-L1 inhibitor, a BRAF inhibitor, a CTLA-4 inhibitor, a MEK inhibitor, an ERK inhibitor, vemurafenib, dacarbazine, trametinib, dabrafenib, durvalumab, an mTOR inhibitor, a CAR-T therapy, abiraterone, enzalutamide, apalutamide, 5-fluorouracil (5-FU), FOLFOX (i.e., folinic acid, 5-fluorouracil, and oxaliplatin), FOLFIRI (i.e., folinic acid, 5-fluorouracil, and irinotecan), herceptin, xeloda, a PD-1 antibody (e.g., pembrolizumab or nivolumab), a PD-L1 antibody, a CTLA-4 antibody (e.g, ipilimumab), ramucirumab, rindopepimut, glembatumumab, vedotin, ANG1005, and/or ANG4043.

In some embodiments of any of the methods of treating cancer, the cancer is a renal cell carcinoma and the antiproliferative is a PD-1 inhibitor, a PD-L1 inhibitor, or an mTOR inhibitor. In other embodiments, the cancer is diffuse large B-cell lymphoma and the antiproliferative is a CAR-T therapy. In certain embodiments, the cancer is prostate cancer and the antiproliferative is abiraterone, enzalutamide, or apalutamide. In some embodiments, the cancer is hepatocellular carcinoma, gastric cancer, or esophageal cancer and the antiproliferative is 5-FU, FOLFOX, FOLFIRI, herceptin, or xeloda. In some embodiments, the cancer is sarcoma and the antiproliferative is gemcitabine. In other embodiments, the cancer is pancreatic cancer and the antiproliferative is irinotecan, cisplatin, abraxane, a taxane (e.g., paclitaxel or docetaxel), or capecitabine.

The methods of treating cancer may further include administering an antiproliferative such as alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelin A receptor antagonist, retinoic acid receptor agonists, immuno-modulators, hormonal and anti-hormonal agents, photodynamic agents, tyrosine kinase inhibitors, antisense compounds, corticosteroids, HSP90 inhibitors, proteosome inhibitors (for example, marizomib), CD40 inhibitors, anti-CSI antibodies, FGFR3 inhibitors, VEGF inhibitors, MEK inhibitors, cyclin D1 inhibitors, NF-kB inhibitors, anthracyclines, histone deacetylases, kinesin inhibitors, phosphatase inhibitors, COX2 inhibitors, mTOR inhibitors, calcineurin antagonists, IMiDs, and/or other agents used to treat proliferative diseases.

In some embodiments of any of the methods of treating cancer, the cancer is breast cancer such as triple negative breast cancer, colon cancer, renal cell cancer, lung cancer (e.g., non-small cell lung cancer), hepatocellular carcinoma, gastric cancer, ovarian cancer, pancreatic cancer, esophageal cancer, prostate cancer, sarcoma, glioblastoma, diffuse large B-cell lymphoma, leukemia (e.g., acute myeloid leukemia), or melanoma. In some embodiments of any of the methods of treating cancer, the cancer is melanoma. In some embodiments of any of the methods of treating cancer, the cancer is breast cancer. In some embodiments of any of the foregoing methods, the cancer is renal cell cancer. In some embodiments of any of the methods of treating cancer, the cancer is pancreatic cancer. In some embodiments of any of the methods of treating cancer, the cancer is non-small cell lung cancer. In some embodiments of any of the methods of treating cancer, the cancer is colon cancer. In some embodiments of any of the methods of treating cancer, the cancer is ovarian cancer. In some embodiments of any of the methods of treating cancer, the cancer is glioblastoma. In some embodiments of any of the methods of treating cancer, the cancer is prostate cancer. In some embodiments of any of the methods of treating cancer, the cancer is diffuse large B-cell lymphoma. In some embodiments, the cancer is leukemia (e.g., acute myeloid leukemia).

In particular embodiments of any of the methods of treating cancer, the cancer is melanoma (e.g., metastatic melanoma) that is resistant to, or has failed to respond to prior treatment with, vemurafenib, dacarbazine, interferon therapy, a CTLA-4 inhibitor, a BRAF inhibitor, a MEK inhibitor, a PD1 inhibitor, a PDL-1 inhibitor, and/or a CAR-T therapy. In some embodiments of any of the methods of treating cancer, the cancer is glioblastoma that is resistant to, or has failed to respond to prior treatment with, temozolimide, radiotherapy, avastin, irinotecan, a VEGFR2 inhibitor, a CAR-T therapy, and/or an mTOR inhibitor. In some embodiments of any of the methods of treating cancer, the cancer is non-small cell lung cancer such as metastatic non-small cell lung cancer (e.g., EGFR-wild type non-small cell lung cancer and/or squamous non-small cell lung cancer) that is resistant to, or has failed to respond to prior treatment with, an EGFR inhibitor, platinum agents (e.g., carboplatin), avastin, an ALK inhibitor, a MET inhibitor, a taxane (e.g., paclitaxel and/or doceltaxel), gemzar, alimta, radiotherapy, a PD-1 inhibitor, a PD-L1 ihibitor, and/or a CAR-T therapy. In some embodiments of any of the methods of treating cancer, the cancer is a breast cancer (e.g., triple negative breast cancer) that is resistant to, or has failed to respond to prior treatment with, herceptin, perjeta, tamoxifen, xeloda, docetaxel, carboplatin, paclitaxel, abraxane, adriamycin, gemcitabine, avastin, halaven, neratinib, a PARP inhibitor, a PD-1 inhibitor, a PD-L1 inhibitor, a CAR-T therapy, apalutamide, and/or an mTOR inhibitor. In some embodiments of any of the methods of treating cancer, the cancer is ovarian cancer (e.g., advanced ovarian cancer) that is resistant to, or has failed to respond to prior treatment with, a PARP inhibitor, avastin, platinum agents such as carboplatin, paclitaxel, docetaxel, topotecan, gemzar, a VEGR2 inhibitor, a folate receptor antagonist, a PD-1 inhibitor, a PD-L1 inhibitor, a CAR-T therapy, demcizumab, and/or fosbretabulin.

In some embodiments of any of the methods of treating cancer, the additional anti-cancer therapy, if present, includes chemotherapy.

In some embodiments of any of the methods of treating cancer, the chemotherapy includes docetaxel. In some embodiments, the method includes administering an effective amount of docetaxel to the subject once every seven days. In some embodiments, the effective amount of docetaxel is at least 28 mg/m$^2$. In some embodiments, the effective amount of docetaxel is about 28 mg/m$^2$ to about 35 mg/m$^2$.

In some embodiments of any of the methods of treating cancer, the additional anti-cancer therapy includes chemotherapy and immunotherapy. In some embodiments of any of the methods of treating cancer, the anti-cancer therapy includes carboplatin or cisplatin, pemetrexed, and pembrolizumab. In some embodiments, the method includes administering to the subject an effective amount of pembrolizumab once every twenty-one days. In some embodiments, the effective amount of pembrolizumab is about 200 mg. In some embodiments, the method includes administering to the subject an effective amount of carboplatin or cisplatin once every twenty-one days. In some embodiments, the effective amount of carboplatin or cisplatin is calculated using the formula: Total dose (mg)=(Target area under the curve)×(subject's glomerular filtration rate+25), wherein the target area under the curve is 4 mg/mL*min to 6 mg/mL*min and the subject's glomerular filtration rate was measured by Cr-EDTA clearance. In some embodiments, the effective amount of carboplatin or cisplatin is about 300 mg/m$^2$ to about 360 mg/m$^2$. In some embodiments, the method includes administering to the subject an effective amount of pemetrexed once every twenty-one days. In some embodiments, the effective amount of pemetrexed is 500 mg/m$^2$. In some embodiments of any of the methods of treating cancer, the method further includes administering to the subject an effective amount of folic acid, vitamin B12, and/or corticosteroids. In some embodiments, the method includes administering to the subject an effective amount of corticosteroids twice per day for three days prior to administration of pemetrexed.

In some embodiments of any of the methods of treating cancer, the method further includes administering to the subject an effective amount of a statin (e.g., rosuvastatin or atorvastatin).

In some embodiments of any of the methods of treating cancer, the method further includes administering to the subject an effective amount of an anti-emetic agent (e.g., ondansetron, granisetron, palonosetron, metoclopramide, haloperidol, dexamethasone, aprepitant, fosaprepitant, lorazepam, dronabinol, prochlorperazine, or chlorpromazine), an anti-diarrheal agent (e.g., an opiate agonist or octreotide), an appetite stimulant (e.g., megestrol acetate, metoclopramide, dronabinol, prednisone, or dexamethasone), a general stimulant, a bisphosphonate (e.g., etidronate, clodronate, tiludronate, pamidronate, neridronate, opladronate, alendronate, ibandronate, risedronate, or zoledronate), a gonadotrophin releasing hormone agonist (e.g., buserelin, histrelin, leuprorelin, triptorelin, goserelin, or nafarelin), and/or growth factors (e.g., filgrastim).

In some embodiments of any of the methods of treating cancer, the cancer is resistant to an anti-cancer therapy (e.g., platinum-containing chemotherapy, a PD-1 inhibitor, a PD-L1 inhibitor, a CTLA-4 inhibitor, an antimitotic agent, a topoisomerase inhibitor, an antimetabolite, an angiogenesis inhibitor, a kinase inhibitor, and/or an alkylating agent). In some embodiments of any of the methods of treating cancer, the cancer progressed on or after treatment with an anti-cancer therapy (e.g., platinum-containing chemotherapy, a PD-1 inhibitor, a PD-L1 inhibitor, an angiogenesis inhibitor, a kinase inhibitor, and/or an alkylating agent). In some embodiments of any of the methods of treating cancer, the cancer has been determined to be, or is predicted to be, resistant to an anti-cancer therapy (e.g., a PD-1 inhibitor, a PD-L1 inhibitor, a CTLA-4 inhibitor, a topoisomerase inhibitor, an antimetabolite, an angiogenesis inhibitor, a kinase inhibitor, and/or an alkylating agent).

In some embodiments of any of the methods of treating cancer, the cancer has a PD-L1 expression level of less than 1% when tested in an immunohistochemistry assay (e.g., an immunohistochemistry assay with a tumor proportion score). In some embodiments of any of the methods of treating cancer, the cancer has a PD-L1 expression level of about 1% when tested in an immunohistochemistry assay (e.g., an immunohistochemistry assay with a tumor proportion score). In some embodiments of any of the methods of treating cancer, the cancer has a PD-L1 expression level of about 1% to about 49% (e.g., about 1% to about 20%, about 5% to about 30%, about 15% to about 40%, about 25% to about 49%) when tested in an immunohistochemistry assay (e.g., an immunohistochemistry assay with a tumor proportion score). In some embodiments of any of the methods of treating cancer, the cancer is metastatic and/or locally advanced. In some embodiments of any of the methods of treating cancer, the cancer is unresectable.

Definitions

As used herein, the term "administration" refers to the administration of a composition (e.g., a salt or a preparation that includes a salt as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal, and vitreal.

By "biological sample" or "sample" is meant a fluid or solid sample from a subject. Biological samples may include cells; nucleic acid, protein, or membrane extracts of cells; or blood or biological fluids including (e.g., plasma, serum, saliva, urine, bile). Solid biological samples include samples taken from feces, the rectum, central nervous system, bone, breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, and the thymus. Fluid biological samples include samples taken from the blood, serum, plasma, pancreatic fluid, CSF, semen, prostate fluid, seminal fluid, urine, saliva, sputum, mucus, bone marrow, lymph, and tears. Samples may be obtained by standard methods including, e.g., venous puncture and surgical biopsy. In certain embodiments, the biological sample is a blood, plasma, or serum sample. In some embodiments, the biological sample is a tumor sample from a biopsy.

The term "cancer" refers to any cancer caused by the proliferation of malignant neoplastic cells, such as tumors, neoplasms, carcinomas, sarcomas, leukemias, and lymphomas.

By "determining the level of a cell type" is meant the detection of a cell type by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third party laboratory that directly acquired the physical entity or value). Methods to measure cell levels generally include, but are not limited to, flow cytometry and immunohistochemistry. Exemplary methods are provided herein. In some embodiments of any of the foregoing methods, the level of MDSCs and/or activated T-cells may be determined as described in Iclozan et al. Cancer Immunol. Immunother. 2013, 62(5): 909-918. In some embodiments of any of the foregoing methods, the level of MDSCs and/or activated T-cells may be determined as described in Kitano et al. Cancer Immunol. Res. 2014, 2(8); 812-821.

A cancer "determined to be drug resistant," as used herein, refers to a cancer that is drug resistant, based on unresponsiveness or decreased responsiveness to a chemotherapeutic agent, or is predicted to be drug resistant based on a prognostic assay (e.g., a gene expression assay).

By a "drug resistant" cancer is meant a cancer that does not respond, or exhibits a decreased response to, one or more chemotherapeutic agents (e.g., any agent described herein).

The term "effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "effective amount" does not in fact require successful treatment be achieved in a particular individual. Rather, an effective amount may be that amount that provides a particular desired pharmacological response in a significant number of subjects when administered to patients in need of such treatment. It is specifically understood that particular subjects may, in fact, be "refractory" to an "effective amount." To give but one example, a refractory subject may have a low bioavailability such that clinical efficacy is not obtainable. In some embodiments, reference to an effective amount may be a reference to an amount as measured in one or more specific tissues (e.g., a tissue affected by the disease, disorder or condition) or fluids (e.g., blood, saliva, serum, sweat, tears, urine). Those of ordinary skill in the art will appreciate that, in some embodiments, an effective amount may be formulated and/or administered in a single dose. In some embodiments, an effective amount may be formulated and/or administered in a plurality of doses, for example, as part of a dosing regimen.

As used herein, the term "failed to respond to a prior therapy" or "refractory to a prior therapy," refers to a cancer that progressed despite treatment with the therapy.

By "level" is meant a level of a cell type, as compared to a reference. The reference can be any useful reference, as defined herein. By a "decreased level" or an "increased level" of a cell type is meant a decrease or increase in cell level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a cell type may be expressed in mass/vol (e.g., g/dL, mg/mL, µg/mL, ng/mL) or percentage relative to total cells in a sample. In some embodiments of any of the foregoing methods, the reference is a sample from a healthy subject such as a subject that does not have cancer. In some embodiments of any of the foregoing methods, the reference is an artificial sample with a level (e.g., a level of MDSCs such as monocytic and/or granulocytic MDSCs or activated T-cells) shown beneficial in the treatment of a disorder.

As used herein, "metastatic nodule" refers to an aggregation of tumor cells in the body at a site other than the site of the original tumor.

As used herein, "metastatic tumor" refers to a tumor or cancer in which the cancer cells forming the tumor have a high potential to or have begun to, metastasize, or spread from one location to another location or locations within a subject, via the lymphatic system or via haematogenous spread, for example, creating secondary tumors within the subject. Such metastatic behavior may be indicative of malignant tumors. In some cases, metastatic behavior may be associated with an increase in cell migration and/or invasion behavior of the tumor cells.

Examples of cancers that can be defined as metastatic include but are not limited to lung cancer (e.g., non-small cell lung cancer), breast cancer, ovarian cancer, colorectal cancer, biliary tract cancer, bladder cancer, brain cancer including glioblastomas and medullablastomas, cervical cancer, choriocarcinoma, endometrial cancer, esophageal cancer, gastric cancer, hematological neoplasms, multiple myeloma, leukemia, intraepithelial neoplasms, liver cancer, lymphomas, neuroblastomas, oral cancer, pancreatic cancer, prostate cancer, sarcoma, skin cancer including melanoma, basocellular cancer, squamous cell cancer, testicular cancer, stromal tumors, germ cell tumors, thyroid cancer, and renal cancer.

"Non-metastatic cell migration cancer" as used herein refers to cancers that do not migrate via the lymphatic system or via haematogenous spread.

As used herein, the term "pharmaceutical composition" refers to an active compound, or pharmaceutically acceptable salt thereof, formulated together with one or more pharmaceutically acceptable carriers. In some embodiments, active compound or salt is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

A "pharmaceutically acceptable excipient," as used herein, refers any inactive ingredient (for example, a vehicle capable of suspending or dissolving the active compound) having the properties of being nontoxic and non-inflammatory in a subject. Typical excipients include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration.

The term "pharmaceutically acceptable salt," as use herein, refers to those salts of the compounds described here that are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Handbook of Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

"Progression-free survival" as used herein, refers to the length of time during and after medication or treatment during which the disease being treated (e.g., cancer) does not get worse.

"Proliferation" as used in this application involves reproduction or multiplication of similar forms (cells) due to constituting (cellular) elements.

As used herein, "slowing the spread of metastasis" refers to reducing or stopping the formation of new loci; or reducing, stopping, or reversing the tumor load.

The term "subject," as used herein, refers to a human or non-human animal (e.g., a mammal such as a non-human primate, horse, cow, or dog).

The term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

A "therapeutic regimen" refers to a dosing regimen whose administration across a relevant population is correlated with a desired or beneficial therapeutic outcome.

The term "treatment" (also "treat" or "treating"), in its broadest sense, refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The term "PD-1 inhibitor," as used herein, refers to a compound such as an antibody capable of inhibiting the activity of the protein that in humans is encoded by the PDCD1 gene. Known PD-1 inhibitors include nivolumab, pembrolizumab, pidilizumab, BMS 936559, and atezolizumab.

The term "PD-L1 inhibitor," as used herein, refers to a compound such as an antibody capable of inhibiting the activity of the protein that in humans is encoded by the CD274 gene. Known PD-L1 inhibitors include atezolizumab and durvalumab.

The term "CTLA-4 inhibitor," as used herein, refers to a compound such as an antibody capable of inhibiting the activity of the protein that in humans is encoded by the CTLA4 gene. Known CTLA-4 inhibitors include ipilimumab.

The term "CSF-1R inhibitors," as used herein refers to a compound such as an antibody capable of inhibiting the activity of the protein that in humans is encoded by the CSF1R gene. Known CSF-1R inhibitors include pexidartinib and 4-(2,4-difluoroanilino)-7-ethoxy-6-(4-methylpiperazin-1-yl)quinoline-3-carboxamide.

The term "IDO inhibitor," as used herein, refers to a compound such as an antibody capable of inhibiting activity of the protein that in humans is encoded by the IDO1 gene. Known IDO inhibitors include norharmane, rosmarinic acid, and alpha-methyl-tryptophan.

The term "A1 adenosine inhibitor," as used herein, refers to a compound such as an antibody capable of inhibiting the activity of the protein that in humans is encoded by the ADORA1 gene. Known A1 adenosine inhibitors include 8-cyclopentyl-1,3-dimethylxanthine, 8-cyclopentyl-1,3-dipropylxanthine, 8-phenyl-1,3-dipropylxanthine, bamifylline, BG-9719, tonapofylline, FK-453, FK-838, rolofylline, and N-0861.

The term "A2A adenosine inhibitor," as used herein, refers to a compound such as an antibody capable of inhibiting the activity of the protein that in humans is encoded by the ADORA2A gene. Known A2A adenosine inhibitors include ATL-4444, istradefylline, MSX-3, preladenant, SCH-58261, SCH-412,348, SCH-442,416, 2-butyl-9-methyl-8-(triazol-2-yl)purin-6-amine, VER-6623, VER-6947, VER-7835, viadenant, and ZM-241,385.

The term "A2B adenosine inhibitor," as used herein, refers to a compound such as an antibody capable of inhibiting the activity of the protein that in humans is encoded by the ADORA2B gene. Known A2B adenosine inhibitors include N-[5-(1-cyclopropyl-2,6-dioxo-3-propyl-7H-purin-8-yl)pyridin-2-yl]-N-ethylpyridine-3-carboxamide, 3-ethyl-1-propyl-8-[1-[[3-(trifluoromethyl)phenyl]methyl]pyrazol-4-yl]-7H-purine-2,6-dione, MRS-1706, MRS-1754, N-[2-[[2-phenyl-6-[4-(3-phenylpropyl)piperazine-1-carbonyl]-7H-pyrrolo[2,3-d]pyrimidin-4-yl]amino]ethyl]acetamide, PSB-603, PSB-0788, and PSB-1115.

The term "A3A adenosine inhibitor," as used herein, refers to a compound such as an antibody capable of inhibiting the activity of the protein that in humans is encoded by the ADORA3 gene. Known A3A adenosine inhibitors include KF-26777, MRS-545, MRS-1191, MRS-1220, MRS-1334, MRS-1523, MRS-3777, MRE-3005-F20, MRE-3008-F20, PSB-11, OT-7999, VUF-5574, and SSR161421.

The term "arginase inhibitor," as used herein, refers to a compound capable of inhibiting the activity of a protein that in humans is encoded by the ARG1 or ARG2 genes. Known arginase inhibitors include (2s)-(+)-amino-5-iodoacetamidopentanoic acid, NG-hydroxy-L-arginine, (2S)-(+)-amino-6-iodoacetamidohexanoic acid, and (R)-2-amino-6-borono-2-(2-(piperidin-1-yl)ethyl)hexanoic acid.

The term "HDAC inhibitor," as used herein, refers to a compound such as an antibody that is capable of inhibiting the activity of the protein that is a member of the histone deacetylase class of enzymes, e.g., HDAC1, HDAC2, HDAC3, HDAC4, HDAC5, HDAC6, HDAC7, HDAC8, HDAC9, HDAC10, HDAC11, SIRT1, SIRT2, SIRT3, SIRT4, SIRT5, SIRT6, and SIRT7. Known HDAC inhibitors include valproic acid, SAHA, and romidepsin.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

DETAILED DESCRIPTION OF THE INVENTION

Figure 1:
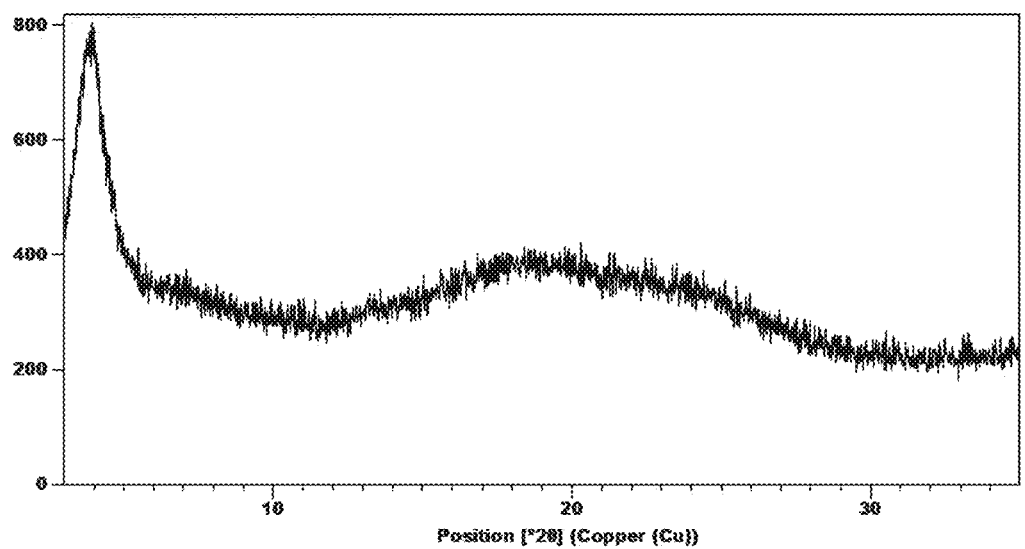
FIG. 1 is an XRPD diffractogram of an amorphous zinc salt of 2-[3-[(3R)-3-[[2-chloro-3-(trifluoromethyl)phenyl]methyl-(2,2-diphenylethyl)amino]butoxy]phenyl]acetic acid (Compound 1) prepared using zinc chloride as the counterion source.

To identify salts of 2-[3-[(3R)-3-[[2-chloro-3-(trifluoromethyl)phenyl]methyl-(2,2-diphenylethyl)amino]butoxy]phenyl]acetic acid (Compound 1), an LXR agonist, having improved processability and stability, the present inventors carried out extensive salt screening experiments with over 65 different counterion sources and solvent systems prepared from over 15 solvents or solvent mixtures.

In an initial screen of common counterion sources, the only salts prepared in apparent crystalline form were those prepared with hydrochloric acid, DL-mandelic acid, and naphthalene sulfonic acid, the hydrochloride salt being the only salt that could be reproduced and scaled up. However, it was found that the hydrochloride salt, along with several strong acid salts (i.e., $H_2SO_4$, HBr, p-toluenesulfonic acid, and methanesulfonic acid salts), were prone to instability, e.g., the strong acid salts were found to readily undergo apparent esterification with alcoholic solvents. Subsequent investigations into salts prepared with weak acids, e.g., oleic acid, octanoic acid, and acetic acid, resulted in isolation of only the free compound.

Further, the inventors found that the hydrochloride salt was not stable under vacuum and moderate to high temperature (e.g., above 50° C.). Under these conditions, the hydrochloride salt was prone to discoloration and/or loss of hydrochloric acid. The inventors also found that extraction of the hydrochloride salt with water led to loss of hydrochloric acid creating further processing difficulties. The hydrochloride salt was further found to undergo apparent esterification in the presence of free alcohol groups, e.g., when in alcoholic solvents or in formulations with excipients with free alcohol groups such as sorbitol, or esterification in the presence of lipophilic esters such as linoleate. These instability issues of the hydrochloric acid salt made it less suitable for processing into a drug product, thus salt screening studies were conducted to find a more suitable salt form.

Subsequent salt screening studies were performed to identify counterions and solvent systems that were conducive to forming salts that possess both improved physical properties and stability. From these salt screening studies, including experiments with over sixty-five different counter ion sources, it was found that the 2:1 (Compound 1:zinc) salt was, surprisingly, one of the minority of salts that formed as a stable solid as opposed to the gels, gums, oils, and semi-solids which formed with the majority of counterion sources. As a reproducible flowable solid, the 2:1 (Compound 1:zinc) salt is much more suitable for scale up and development in a drug product.

2-[3-[(3R)-3-[[2-chloro-3-(trifluoromethyl)phenyl]methyl-(2,2-diphenylethyl)amino]butoxy]phenyl] acetic acid 2-[3-[(3R)-3-[[2-chloro-3-(trifluoromethyl)phenyl]methyl-(2,2-diphenylethyl)amino]butoxy]phenyl] acetic acid (Compound 1) is an LXRβ agonist having the structure Compound 1

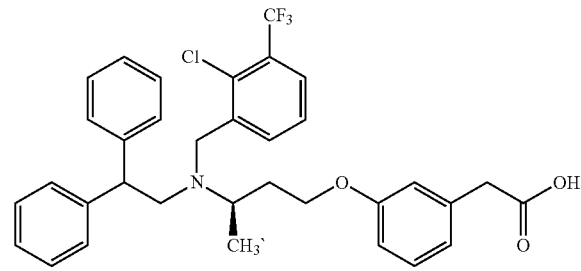

Compound 1-mediated activation of the LXR signaling pathway has been shown to induce expression of ApoE, which functions as a tumor suppressor by virtue of its ability to regulate key features of tumorigenesis. Compound 1 has a higher specificity for the LXRβ isoform. These features include suppression of cancer cell invasion (~45% in vitro), inhibition of endothelial recruitment (~50% in vitro) and the reduction of MDSCs in circulation (~40%) and in tumors (>60%). In in vitro studies, Compound 1 induced ApoE gene expression by 3-fold in cancer cells and up to 40-fold in human peripheral blood mononuclear cells (hPBMCs) compared to control cells. The $EC_{50}$ of Compound 1 for ApoE induction was 385 nM in cancer cells and 271 nM in hPBMCs.

In syngeneic and human xenograft mouse tumor models of melanoma (harboring different genetic backgrounds), glioblastoma, TNBC, ovarian cancer, and lung cancer, Compound 1 inhibited primary tumor growth by 48-95%. Extent of tumor growth inhibition varied with model. In a mouse model of TNBC metastasis, Compound 1 inhibited metastatic spread of cancer cells by ~ 9-fold. Moreover, the anti-tumor activity of Compound 1 in combination with an anti-PD-1 antibody inhibited tumor growth by >80% in a syngeneic mouse melanoma model that is otherwise not responsive to anti-PD-1 antibody. Furthermore, inhibition of tumor growth in the same syngeneic mouse melanoma model was superior when the mice received combination therapy of Compound 1 and anti-CTLA-4 antibody relative to either therapy alone. Similarly, in a syngeneic mouse melanoma model, Compound 1 demonstrated superior anti-tumor efficacy in combination with dacarbazine (>80%), compared to either treatment alone. In tumor growth studies, minimum efficacious doses ranged from 25-40 mg/kg/day administered orally (PO) resulting in exposures that ranged from 10,000-50,000 ng-h/mL.

In safety pharmacology assessments, Compound 1 produced a significant increase, but not inhibition of human ether-à-go-go-related gene (hERG) channel conductance in an in vitro hERG assay. There were no Compound 1-related effects on qualitative electrocardiogram (ECG) parameters (PR or QTc intervals or QRS duration) in dogs, but there was a dose related decrease in mean heart rate at the Day 1 post-dose interval that was significantly different in females following the 150 (stepped down to 100) mg/kg/day dose. This change was not observed during the recovery period and was not considered adverse. Furthermore, no adverse effects were noted during the neurobehavioral functional observation battery (FOB) or respiratory evaluations in rats. Given the favorable safety profile of Compound 1 at the highest doses tested in the repeat dose toxicity studies, the potential for cardiovascular, respiratory or central nervous system (CNS) system effects is considered low.

In oral PK studies, Compound 1 was well absorbed in CD-1 mice with a calculated absolute oral bioavailability (% F) often >100%, indicative of possible enterohepatic recycling of parent compound. The time to maximum plasma concentration (Tmax) was similar for males and females and ranged from 2 to 8 hours. The mean apparent oral half-life (t½) ranged from 6.5-8 hours in mice. There was a significant food effect showing that Compound 1 plasma concentrations were >2-fold higher when administered to mice in the fed state. In Sprague-Dawley rats, the combined, mean % F (following a 30 mg/kg oral dose of 2-[3-[(3R)-3-[[2-chloro-3-(trifluoromethyl)phenyl]methyl-(2,2-diphenylethyl)amino]butoxy]phenyl]acetic acid) was moderate (~31%), and Tmax was similar for males and females, ranging from 4 to 8 hours. Compound 1 was cleared at a lower rate in female rats compared to males, which resulted in higher systemic exposure to Compound 1 in females at all dose levels tested. The mean apparent oral t % in female rats was 6.5 hours (not calculable in males). In male Beagle dogs given an oral dose of Compound 1, Tmax ranged from 4-8 hours. The mean % F was moderate (18-30% depending on dose and formulation) and mean apparent oral t % ranged from 5-6.7 hours. In Cynomolgus monkeys, mean % F was low to moderate (6-19% depending on dose and formulation). Following an oral dose, monkeys had a mean Tmax of 4 hours. Mean oral t % ranged from 5.5-8 hours.

Compound 1 is subjected to phase I and phase II metabolism, which includes oxidation, dealkylation, glucuronidation and combinations thereof. In vitro, Compound 1 is metabolized predominantly by the cytochrome P450 (CYP) isoform CYP3A4, but it is also a substrate for CYP2E1, CYP2C9, CYP2C19, and possibly CYP2J2. While Compound 1 is not a strong inhibitor of any human CYP450s in vitro, it is a moderate inhibitor of CYP2C8 (7.5 μM 50% inhibitory concentration [IC50]) and a weak inhibitor of 2B6 (15 μM IC50). Compound 1 very weakly inhibited 1A1, 2A6, 2C9, 2C19, 2D6, 2E1, and 3A4 in vitro, but CYP3A time-dependent inhibition (TDI) was demonstrated in vitro using testosterone as the substrate. Induction of CYP3A by Compound 1 was demonstrated in primary cultures of cryopreserved hepatocytes (2 donors) and the potential of Compound 1 to induce CYP2B6 cannot be ruled out (1 concentration in 1/3 donors was induced >2-fold). Compound 1 did not induce CYP1A2. In efflux transporters, Compound 1 does not inhibit P-glucoprotein (P-gp) but does inhibit breast cancer resistance protein (BCRP) transport in vitro (55% at 5 μM). Compound 1 is a potent inhibitor of the uptake transporter organic anion transporting polypeptide (OATP) 1B1 in vitro (0.099 μM IC50). Compound 1 also appears to be a moderate inhibitor of OATP1B3 (3.7 μM IC50). Compound 1 only weakly inhibited OAT1, OAT3, and OCT2 in vitro with inhibition less than 50% at 50 μM.

Potential risks with Compound 1 in the clinical setting based on animal toxicology studies include elevations in serum cholesterol and TG, neutropenia/leukopenia, nausea and/or vomiting, elevations in liver enzymes, development or worsening of cataracts, cardiac rhythm disturbances and/or reduced cardiac function, harderian gland adenocarcinoma, and/or generalized edema.

Nivolumab

Nivolumab is a fully human immunoglobulin (Ig) G4 monoclonal antibody directed against the negative immunoregulatory human cell surface receptor programmed death-1 (PD-1) with immune checkpoint inhibitory and antineoplastic activities. Nivolumab binds to and blocks the activation of PD-1, an Ig superfamily transmembrane protein, by its ligands programmed cell death ligand 1 (PD-L1), overexpressed on certain cancer cells, and programmed cell death ligand 2 (PD-L2), which is primarily expressed on Antigen Presenting Cells. This results in the activation of T-cells and cell-mediated immune responses against tumor cells or pathogens. Activated PD-1 negatively regulates T-cell activation and plays a key role in tumor evasion from host immunity. The nivolumab dose will be 240 mg administered as an intravenous infusion over 60 minutes on Days 1 and 15 of each 28-day cycle.

There is potential for overlapping toxicities between Compound 1 and nivolumab. Specifically, a DLT of Grade 4 neutropenia has been seen on Compound 1 single agent therapy and myelosuppression may be observed with nivolumab treatment. The pharmacological effects of Compound 1 include modulation of sterol biosynthesis. Consequently, hyperlipidemia has been observed in subjects treated with Compound 1, which has also been reported in subjects treated with nivolumab. Liver function abnormalities have been observed in pre-clinical toxicity studies with Compound 1 and immune-mediated hepatitis has been observed with nivolumab treatment.

Ipilimumab

Ipilimumab is a recombinant human IgG1 kappa monoclonal antibody that binds to the cytotoxic T-lymphocyte-associated protein 4 (CTLA-4). CTLA-4 is a negative regulator of T-cell activity. By binding to CTLA-4, ipilimumab blocks the interaction of CTLA-4 with its ligands, CD80/CD86. Blockade of CTLA-4 has been shown to augment T-cell activation and proliferation, including the activation and proliferation of tumor infiltrating T-effector cells. Inhibition of CTLA-4 signaling can also reduce T-regulatory cell function, which may contribute to a general increase in T cell responsiveness, including the anti-tumor immune response.

In some embodiments, the ipilimumab dose is 3 mg/kg administered as an IV infusion on Day 1 of each 28-day cycle for a maximum of 4 doses.

There is potential for overlapping toxicities between Compound 1 and ipilimumab. Liver function abnormalities have been observed in pre-clinical toxicity studies with Compound 1; immune-mediated hepatitis has been observed with ipilimumab treatment.

Docetaxel

Docetaxel is an antineoplastic agent belonging to the taxoid family. It is prepared by a semi-synthesis beginning with a precursor extracted from the renewable needle biomass of yew plants. The chemical name for docetaxel is (2R,3S)—N-carboxy-3-phenylisoserine,N-tert-butyl ester, 13-ester with 5b-20-epoxy-1,2a,4,7b, 10b, 13a-hexahy-droxytax-11-en-9-one 4-acetate 2-benzoate, trihydrate.

In some embodiments, the docetaxel is administered as an IV infusion on days 1, 8, and 15 of each 28-day cycle. In some embodiments, the docetaxel dose was 35 mg/m$^2$. In some embodiments, 28 mg/m$^2$ is the docetaxel dose.

There is potential for overlapping toxicities between Compound 1 and docetaxel. Specifically, a DLT of Grade 4 neutropenia has been seen on Compound 1 single agent therapy and myelosuppression may be observed with docetaxel treatment. Liver function abnormalities have been observed in pre-clinical toxicity studies with Compound 1; hepatotoxicity has been observed with docetaxel treatment.

Pembrolizumab

Pembrolizumab is a programmed death receptor-1 (PD 1)-blocking antibody. Pembrolizumab is a humanized monoclonal IgG4 kappa antibody with an approximate molecular weight of 149 kDa. Pembrolizumab is produced in recombinant Chinese hamster ovary (CHO) cells.

In some embodiments, pembrolizumab is administered as a dose of 200 mg using a 30 minutes IV infusion on Day 1 of each 21 days cycle after all procedures and assessments have been completed and prior to the administration of other drugs, and with a gap of 30 minutes between the administration of next drug.

Carboplatin

The chemical name for carboplatin, USP is platinum, diamine[1,1-cyclobutanedicarboxylato(2-)-O,O']-(SP-4-2). Carboplatin, USP is a crystalline powder. It is soluble in water at a concentration of approximately 14 mg/mL, and the pH of a 1% solution is 5-7. It is virtually insoluble in ethanol, acetone, and dimethylacetamide. Carboplatin produces predominantly interstrand DNA cross-links rather than DNA-protein cross-links. This effect is apparently cell cycle nonspecific. Carboplatin induce equal numbers of drug-DNA cross-links, causing equivalent lesions and biological effects.

In some embodiments, the initial dose of carboplatin injection is determined by the use of mathematical formulae, which is based on a subject's pre-existing renal function or renal function and desired platelet nadir (as renal excretion is the major route of elimination for carboplatin). The use of dosing formulae, as compared to empirical dose calculation based on body surface area, allows compensation for subject variations in pretreatment renal function that might otherwise result in either underdosing (in subjects with above average renal function) or overdosing (in subjects with impaired renal function).

A simple formula for calculating dosage, based upon a subject's glomerular filtration rate (GFR in mL/min) and carboplatin injection target area under the concentration versus time curve (AUC in mg/mL·min), has been proposed by Calvert. In these studies, GFR was measured by Cr-EDTA clearance. The Calvert formula for carboplatin dosing is as follows:

$$\text{Total Dose (mg)} = (\text{target AUC}) \times (\text{GFR} + 25)$$

Note that with this formula, the total dose of carboplatin is calculated in mg, not mg/m². The target AUC of 4 mg/mL·min to 6 mg/mL·min using single agent carboplatin appears to provide the most appropriate dose range in previously treated subjects. This study also showed a trend between the AUC of single agent carboplatin administered to previously treated subjects and the likelihood of developing toxicity.

Pemetrexed

Pemetrexed (for injection) is a folate analog metabolic inhibitor. The drug substance, pemetrexed disodium heptahydrate, has the chemical name L-glutamic acid, N-[4-[2-(2-amino-4,7-dihydro-4-oxo-1H-pyrrolo[2,3-d]pyrimidin-5-yl)ethyl]benzoyl]-, disodium salt, heptahydrate with a molecular formula of $C_{20}H_{19}N_5Na_2O_6 \cdot 7H_2O$ and a molecular weight of 597.49 g/mol.

Pemetrexed exerts its antineoplastic activity by disrupting the folate-dependent metabolic processes essential for cell replication. In vitro studies have shown that pemetrexed behaves as a multitargeted antifolate by inhibiting thymidylate synthase (TS), dihydrofolate reductase (DHFR), and glycinamide ribonucleotide formyltransferase (GARFT) which are crucial for the de novo biosynthesis of thymidine and purine nucleotides. Polyglutamated metabolites of pemetrexed with prolonged intracellular half-life result in prolonged pemetrexed drug action in malignant cells.

In some embodiments, the pemetrexed dose is 500 mg/m² on Day 1 of each 21-day cycle for a maximum of 4 cycles. In some embodiments, subjects treated with pemetrexed must be instructed to take folic acid and vitamin B12 as a prophylactic measure to reduce treatment-related hematologic and GI toxicity. In some embodiments, subjects may also be prescribed with corticosteroids to take 2 times a day for 3 days, beginning the day before each treatment with pemetrexed.

There is potential for overlapping toxicities between Compound 1, pemetrexed, and carboplatin. Specifically, a DLT of Grade 4 neutropenia has been seen on Compound 1 single agent therapy and myelosuppression may be observed with pemetrexed combination treatment with Compound 1 and carboplatin.

Adverse Events

An adverse event (AE) is any untoward medical occurrence in a subject or clinical investigation subject administered a pharmaceutical product, and which does not necessarily have to have a causal relationship with this treatment. An AE can therefore be any unfavorable and unintended sign (including abnormal laboratory findings), symptom, or disease temporally associated with the use of an investigational product, whether or not related to the investigational product.

Death and progressive disease (PD) are not considered AEs. Death is considered an outcome of one or more primary AEs, and PD is considered a worsening of underlying disease. Preexisting conditions (present before the start of the AE collection period) are considered concurrent medical conditions and not AEs. However, a worsening or complication of such a concurrent condition is an AE.

An AE or suspected adverse reaction is considered serious if it results in death; is life threatening, i.e., the subject was at immediate risk of death from the reaction as it occurred but does not include a reaction which hypothetically might have caused death had it occurred in a more severe form; requires in-subject hospitalization or prolongation of existing hospitalization; results in persistent or significant disability/incapacity; is a congenital anomaly/birth defect; or is an important medical event.

Methods of Treatment

The methods described here can be used to treat cancer.

Treating cancer can result in a reduction in size or volume of a tumor. For example, after treatment, tumor size is reduced by 5% or greater (e.g., 10%, 20%, 30%, 40%, 50%, 60%, 70%, 80%, 90% or greater) relative to its size prior to treatment. Size of a tumor may be measured by any reproducible means of measurement. The size of a tumor may be measured as a diameter of the tumor or by any reproducible means of measurement.

Treating cancer may further result in a decrease in number of tumors. For example, after treatment, tumor number is reduced by 5% or greater (e.g., 10%, 20%, 30%, 40%, 50%, 60%, 70%, 80%, 90% or greater) relative to number prior to treatment. Number of tumors may be measured by any reproducible means of measurement. The number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. The number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with the compound of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with the compound of the invention. A decrease in the mortality rate of a population may also be measured, for example, by calculating for a population the average number of disease-related deaths per unit time following completion of a first round of treatment with the compound of the invention.

Treating cancer can also result in an increased average progression-free survival time of a population of treated subjects in comparison to an untreated population. For example, the average progression-free survival time is increased by more than 30 days (more than 60 days, 90 days, or 120 days). An increase in average progression-free survival time of a population may be measured by any reproducible means. An increase in average progression-free survival time of a population may be measured, for example, by calculating for a population the average length of progression-free survival following initiation of treatment with the compound of the invention. An increase in average progression-free survival time of a population may also be measured, for example, by calculating for a population the average length of progression-free survival following completion of a first round of treatment with the compound of the invention.

Compositions

Within the scope of this invention is a composition that contains a suitable carrier and one or more of the therapeutic agents described above.

As described above, the pharmaceutical compositions of the present invention additionally include a pharmaceutically acceptable excipient, which, as used herein, includes any and all solvents, diluents, or other liquid vehicle, dispersion or suspension aids, surface active agents, isotonic agents, thickening or emulsifying agents, preservatives, solid binders, and lubricants, as suited to the particular dosage form desired. Remington's Pharmaceutical Sciences, Sixteenth Edition, E. W. Martin (Mack Publishing Co., Easton, Pa., 1980) discloses various excipients used in formulating pharmaceutical compositions and known techniques for the preparation thereof. Except insofar as any conventional excipient is incompatible with the compounds of the invention, such as by producing any undesirable biological effect or otherwise interacting in a deleterious manner with any other component(s) of the pharmaceutical composition, its use is contemplated to be within the scope of this invention.

The above-described compositions, in any of the forms described above, can be used for treating cancer, or any other disease or condition described herein. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent.

A composition for oral administration can be any orally acceptable dosage form including capsules, tablets, emulsions and aqueous suspensions, dispersions, and solutions. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally include one or more excipients or diluents. In some preferred embodiments, the topical formulations include a material that would enhance absorption or penetration of the active agent(s) through the skin or other affected areas.

Combination Therapies

In some embodiments of the methods described herein, the pharmaceutical composition may further include an additional compound having antiproliferative activity.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures (e.g., surgery and/or radiation therapy). The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

EXAMPLES

Example 1. Methods

X-ray Powder Diffraction (XRPD)
Method 1

XRPD analysis was carried out on a PANalytical X'pert pro, scanning the samples between 3 and 35° 2θ. The material was gently ground to release any agglomerates and loaded onto a multi-well plate with Mylar polymer film to support the sample. The multi-well plate was then placed into the diffractometer and analyzed using Cu K radiation (α1λ=1.54060 A; α2=1.54443 A; β=1.39225 A; α1: α2 ratio=0.5) running in transmission mode (step size 0.0130° 2θ) using 40 kV/40 mA generator settings.

Method 2

X-ray powder diffraction patterns were obtained using a Bruker D8 Advance equipped with a Cu Kα radiation source (λ=1.54°A), a 9-position sample holder and a LYNXEYE super speed detector. Samples were placed on zero-background, silicon plate holders.

Polarized Light Microscopy (PLM)

Method 1

The presence of birefringence was determined using an Olympus BX53 polarizing microscope, equipped with a Motic camera and image capture software (Motic Images Plus 3.0). All images were recorded using the 10× or the 20× objective.

Method 2

Samples were analyzed using an Olympus BX53 polarized light microscope equipped with a PAXcam 3 digital microscope camera.

Thermogravimetric/Differential Thermal Analysis (TG/DTA)

Method 1

Approximately 5 mg of material was weighed into an open aluminum pan and loaded into a simultaneous thermogravimetric/differential thermal analyzer (TG/DTA) and held at room temperature. The sample was then heated, under a nitrogen purge, at a rate of 10° C./min from 20° C. to 300° C. during which time the change in sample weight was recorded along with any differential thermal events (DTA).

Method 2

TGA data were collected using a TA Instruments TGA Q500. Typically, samples (~10 mg) were placed in an open, pre-tared aluminum sample pan and scanned from 25 to 300° C. at a rate of 10° C./min using a nitrogen purge at 60 mL/min.

Differential Scanning Calorimetry (DSC)

Method 1

Approximately 5 mg of material was weighed into an aluminum DSC pan and sealed with an aluminum lid. The sample pan was then loaded into a TA Instruments Discovery DSC 2500 differential scanning calorimeter equipped with a RC90 cooler. Once a stable heat-flow response was obtained, the sample and reference were heated/cooled, under a nitrogen purge, by using the following temperature programs and the resulting heat flow response monitored.

Program 1

Heated 20° C. to 260° C. at 10° C./minute held at 260° C. for 3 minutes;

Cooled 260° C. to 20° C. at 10° C./minute, held at 20° C. for 3 minutes;

Heated 20° C. to 260° C. at 10° C./minute held at 260° C. for 3 minutes;

Cooled 260° C. to 20° C. at 10° C./minute, held at 20° C. for 3 minutes. Program 2

Heated 20° C. to 270° C. at 10° C./minute held at 270° C. for 3 minutes;

Cooled 270° C. to 20° C. at 10° C./minute, held at 20° C. for 3 minutes;

Heated 20° C. to 270° C. at 10° C./minute held at 270° C. for 3 minutes;

Cooled 270° C. to 20° C. at 10° C./minute, held at 20° C. for 3 minutes.

Method 2

DSC data were collected using a TA Instruments Q10 DSC. Typically, samples (2-8 mg) were placed in unsealed but covered hermetic alodined aluminum sample pans and scanned from 30 to 300° C. at a rate of 10° C./min under a nitrogen purge of 50 mL/min.

$^1$H Nuclear Magnetic Resonance Spectroscopy ($^1$H-NMR)

Method 1

$^1$H-NMR spectroscopic experiments were performed on a Bruker AV500 (frequency: 500 MHz). Experiments were performed in CDCl$_3$ and each sample was prepared to about 10 mM concentration.

Method 2

Samples were prepared by dissolving the compound in deuterated dimethylsulfoxide with 0.05% (v/v) tetramethylsilane (TMS). Spectra were collected at ambient temperature on a Bruker Avance 300 MHz NMR with TopSpin software. The number of scans was 16 for proton NMR.

$^{19}$F Nuclear Magnetic Resonance Spectroscopy ($^{19}$F-NMR)

$^{19}$F-NMR spectroscopic experiments were performed on a Bruker AV500 (frequency: 470 MHz). Experiments were performed in CDCl$_3$ and each sample was prepared to about 10 mM concentration.

High Performance Liquid Chromatography-Ultraviolet Detection (HPLC-UV)

The HPLC method uses a C18 column with an acetonitrile/water/trifluoroacetic acid gradient.

Dynamic Vapor Sorption (DVS)

Samples are analyzed using an Aquadyne DVS-2 gravimetric water sorption analyzer. The relative humidity is adjusted between 2-95% and the weight of the sample is continuously monitored and recorded.

Karl Fisher (KF)

The apparent water content in samples is determined by Karl Fischer titration using a Mettler Toledo DL39 Coulometric KF Titrator. HYDRANAL-Coulomat AD was used as the titrant. About 20 mg of the solid is used for titration. The analytical parameters are shown in Table 1 below:

TABLE 1

| KF Parameter | Value |
| --- | --- |
| Speed [%] | 40 |
| Mix time [sec] | 10 |
| Auto start | No |
| Blank [µg] | 0 |
| Drift [µg/min] | 5 |
| Calculation | Ug |
| Standby | Yes |
| Initial drift [µg/min] | <10 |
| Initial Potential [mV] | 100 |

Fourier-Transform Infrared Spectroscopy (FTIR)

FTIR analysis was carried out on a Thermo Scientific, NICOLET™ IS™ 10 FTIR Spectrometer with Attenuated Total Reflectance (ATR). Sufficient material was placed on the center of the plate of the spectrometer and the spectra were obtained.

Example 2. Salt Screening

Study 1

A first study was conducted to identify salts of 2-[3-[(3R)-3-[[2-chloro-3-(trifluoromethyl)phenyl]-methyl-(2,2-diphenylethyl)amino]butoxy]phenyl]acetic acid. 26 counterion sources were selected for salt screening of 2-[3-[(3R)-3-[[2-chloro-3-(trifluoromethyl)phenyl]-methyl-(2,2-diphenylethyl)amino]butoxy]phenyl]acetic acid. The counterion sources are listed in Table 2 below:

TABLE 2

List of selected counterion sources for
salt screening experiments in Study 1

| Counterion Source | No. |
|---|---|
| Hydrochloric Acid (HCl) | 1 |
| Sulfuric acid ($H_2SO_4$) | 2 |
| Benzenesulfonic acid ($C_6H_5O_3SH$) | 3 |
| Phosphoric acid ($H_3PO_4$) | 4 |
| Sodium hydroxide (NaOH) | 5 |
| Potassium hydroxide (KOH) | 6 |
| Calcium hydroxide (Ca(OH)$_2$) | 7 |
| Maleic acid | 8 |
| Fumaric acid | 9 |
| L-Arginine | 10 |
| L-Histidine | 11 |
| L-Malic acid | 12 |
| Diethanolamine | 13 |
| Salicylic acid | 14 |
| Benzoic acid | 15 |
| DL-Mandelic acid | 16 |
| Ethylenediamine | 17 |
| Succinic acid | 18 |
| L-Tartaric acid | 19 |
| L-Aspartic acid | 20 |
| L-Lysine | 21 |
| L-Ascorbic acid | 22 |
| Citric acid | 23 |
| Naphthalene-2-sulfonic acid | 24 |
| 1,2-Ethane-disulfonic acid | 25 |
| Hydroiodic acid | 26 |

Among the counterion sources investigated, only three (hydrochloride, DL-mandelic acid, and naphthalene sulfonic acid) afforded crystalline salts, and reproduction and scaling up of the three crystalline salts was successful only for the hydrochloride salt.

Subsequent studies revealed that the hydrochloride salt, as well as other salts prepared from strong acids, e.g., $H_2SO_4$, HBr, p-toluenesulfonic acid, and methanesulfonic acid, were found to be unstable. In particular, these salts react with excipients and/or components of a formulation. This discovery led to investigation into the use of weak acids, e.g., oleic acid, octanoic acid, and acetic acid, as the counterion source, none of which formed salts with 2-[3-[(3R)-3-[[2-chloro-3-(trifluoromethyl)phenyl]-methyl-(2,2-diphenyl-ethyl)amino]butoxy]phenyl]acetic acid.

Study 2

A second study was conducted to identify salts that afforded both improved processability and stability. The 34 counterion sources and 12 solvent conditions investigated in this study are summarized in Tables 3 and 4 below:

TABLE 3

List of selected counterion sources for
salt screening experiments in Study 2
Counterion Source

| | |
|---|---|
| Hydriodic acid | EDTA |
| Naphthalene-2-sulfonic acid | Ethane sulfonic acid |
| 1,2-Ethane disulfonic acid | Pamoic acid |
| Saccharin | Mucic acid |
| L-Arginine | Gentistic acid |
| N-Methylglucamine | Pyroglutamic acid |
| 2-Hydroxyethanesulfonic acid | Ethylenediamine |
| Ethanolamine | Benzathine |
| Procaine hydrochloride salt | 2-Diethylaminoethanol |
| Piperazine | Diethanolamine |
| Triethanolamine | Ammonium hydroxide |
| Diethylamine | Tromethamine |
| Choline hydroxide | Benethamine |
| L-Lysine monohydrate | Calcium hydroxide |

TABLE 3-continued

List of selected counterion sources for
salt screening experiments in Study 2
Counterion Source

| | |
|---|---|
| Zinc chloride | Magnesium hydroxide |
| 1,5-Naphthalene disulfonic acid | Aluminum hydroxide |
| Nitric acid | Diethylaminoethanol |

TABLE 4

List of selected solvent conditions for
salt screening experiments in Study 2
Solvent and Solvent Mixtures Isopropanol (IPA)
Tetrahydrofuran (THF)
Dichloromethane (DCM)
Ethyl acetate (EtOAc)
Heptane (Hep)
Tert-Butylmethyl ether (TBME)
Water ($H_2O$)
1,4-Dioxane
Acetone
THF:$H_2O$ (9:1)
Acetone:$H_2O$ (9:1)
IPA:$H_2O$ (95:5)

An initial solubility assessment was conducted in 12 solvents/solvent mixtures using amorphous Compound 1. Dissolution was observed in most of the samples. Salt screening by cooling, anti-solvent addition, maturation, liquid assisted grinding, neat grinding and evaporation were all investigated. Gums isolated were subjected to heat/cool maturation cycles (room temperature/50° C.), sonication, prolonged storage under vacuum, prolonged storage at 40° C./75% RH, trituration with anti-solvent and liquid assisted grinding (LAG) with water. From extensive salt screening, eight hits were obtained. Amorphous hits with a high glass transition temperature (Tg) were identified from zinc chloride, naphthalene-2-sulfonic acid, 1,5-naphthalene disulfonic acid, and ethane sulfonic acid. One crystalline hit was identified from ethane sulfonic acid. Poorly crystalline material was isolated from calcium hydroxide, magnesium hydroxide and aluminum hydroxide.

As limited characterization was performed on the isolated hits, focused screens were conducted on the most promising counterions: calcium hydroxide, aluminum hydroxide, ethane sulfonic acid and naphthalene-2-sulfonic acid. Calcium hydroxide and aluminum hydroxide were selected to assess if the initial hits isolated via counterion exchange were single metal or mixed metal salts. Solids isolated from the additional screening were consistent with the initial hits. From additional screening, these samples were likely to be single metal salts. As these hits were not mixed salts, a limited mixed metal screen was performed using magnesium hydroxide and calcium hydroxide. These attempts were unsuccessful. Ethane sulfonic acid and naphthalene-2-sulfonic acid were selected for further screening. However, the initial hits were not reproduced in the further screening attempts. Amorphous solids were isolated, however, the Tg was lower than the Tg of both the free compound (32° C.) and HCl salt (~70-75° C.).

The zinc salt was isolated using the following procedure:
Compound 1 (~250 mg) was dissolved in THF (5 vol) at RT. The solution was dispensed into HPLC vials (75 µl, ca. 15 mg in solution). The solution was held at 50° C. for 5 minutes, observations were recorded. The sample was treated with 1.0 eq. of sodium then the selected equivalent of counter-ion (0.5 eq. of zinc chloride. The sample was held at 50° C. for 10 minutes then cooled to 5° C. at 0.1° C./min. The resulting solution was held at 5° C. overnight then stored at −20° C. After 5 days, the sample remained as a solution and was allowed to evaporate at ambient conditions. A gum was obtained post evaporation and was treated with 10 vol of heptane, followed by sonication for 2 hours. The solid collected was analyzed by XRPD and found to be amorphous.

None of the salts isolated from this study were recommended for development due to long, complex isolation procedures and the propensity of Compound 1 to form gums. However, several salts, e.g., zinc and aluminum, gave encouraging results that suitable salts might be possible and prompted further investigation.

Study 3

A third salt screening study was conducted. Salt formation reactions were attempted at a 100 mg scale using bases with approximate $pK_a$ greater than 8 or acceptable strong acids with a $pK_a$ below 4.

In a first set of salt screening experiments, the counterion sources shown in Table 5 below were investigated.

TABLE 5

List of selected counterion sources for the first set of salt screening experiments in Study 3

| Counterion Source | Molecular Weight (g/mol) | $pKa_1$ |
|---|---|---|
| Ethane-1,2-disulfonic acid | 190.20 | −2.1 |
| Naphthalene-1,5,disulfonic acid | 332.26 | −3.4 |
| Ethanesulfonic acid | 110.13 | −1.6 |
| Nitric acid | 63.02 | −1.3 |
| Naphthalene-2-sulfonic acid | 208.24 | 0.17 |
| Zinc hydroxide | 99.38 | 14 |
| Choline | 121.18 | >11.0 |
| Benzathine | 240.35 | 10.0 |
| Benethamine | 211.30 | 9.4 |
| Ethanolamine | 61.80 | 9.6 |
| Diethanolamine | 105.14 | 9.5 |
| L-Arginine | 174.20 | 9.0 |

Briefly, 2-[3-[(3R)-3-[[2-chloro-3-(trifluoromethyl)phenyl]methyl-(2,2-diphenylethyl)amino]-butoxy]phenyl]acetic acid was suspended/dissolved in six different solvent systems-isopropanol, acetone, cyclohexanone, methyl ethyl ketone, ethyl acetate, and THF. The corresponding counterion source (1.0 equivalents) was then added as a solution (where possible) or via neat addition. Solutions were temperature cycled between two specific temperatures (e.g., 25 and 40° C.). All experiments were monitored for precipitation/crystallization. In vials where crystallization/precipitation was not evident, cooling to sub-ambient temperatures or iterative anti-solvent addition using a suitable anti-solvent was performed, with or without cooling to sub-ambient temperatures (e.g. 5° C.). In vials where crystallization/precipitation was not evident following cooling and/or addition of anti-solvent, the solvent was removed by evaporation. Any solids were isolated by filtration and analyzed by XRPD. Oils or gums were predominantly obtained.

A second salt screen was conducted with the counterion sources shown in Table 6 below.

TABLE 6

List of selected counterion sources for the second set of salt screening experiments in Study 3

| Counterion Source | Molecular Weight (g/mol) | $pKa_1$ |
|---|---|---|
| Sodium edisylate | 234.16 | −2.1 |
| Thiocyanic acid | 59.09 | −1.3 |
| Dioctylsulfosuccinic acid | 422.16 | −0.8 |
| Sodium napsylate | 230.22 | 0.2 |
| Dichloroacetic acid | 128.94 | 1.3 |
| Sodium isethionate | 148.11 | 1.7 |
| Pamoic acid | 388.38 | 2.5 |
| Hippuric acid | 179.18 | 3.6 |
| L-Lysine | 146.19 | 9.2 |
| Histidine | 155.15 | 9.2 |
| 1-(2-Hydroxyethyl)-pyrrolidine | 115.18 | 9.4 |

The procedure for preparing the salts with the counterion sources of Table 5 is as follows. 2-[3-[(3R)-3-[[2-chloro-3-(trifluoromethyl)phenyl]methyl-(2,2-diphenylethyl)amino] butoxy]-phenyl]acetic acid was produced from its hydrochloride salt as per known procedures (Collins et al. J. Med. Chem., 2002, 45:1963-1966). 100 mg of the free material was transferred into 20 mL vials. Ethyl acetate (1 mL) was added to each vial, followed by addition 1.0 eq. of each counterion source. The samples were temperature cycled between ambient temperature and 40° C. in 4-hour cycles with agitation for 24 hours. Heptane was added as an antisolvent to any clear solutions and the samples were placed in the fridge for 24 hours. All solids thus obtained were analyzed by XRPD and all samples that remained as clear solutions were uncapped and left to evaporate. These counterion sources produced solids identified as the counterion sources or sticky, gummy solids.

Another salt screen was conducted using an aqueous precipitative approach. This salt screen used a metathesis procedure where the 1:1 sodium salt of Compound 1 was prepared and 1.0, 0.5, or 0.3 equivalents of the selected metal counterion was added as its chloride or sulfate salt. Alternatively, free Compound 1 was reacted with the selected metal counterion as its acetate or sulfate salt. These aqueous precipitations produced free flowing white solids from zinc, aluminum, and bismuth.

The counterions shown in Table 7 below were investigated.

TABLE 7

List of selected counterion sources for the third set of salt screening experiments in Study 3
Counterion Source

| Counterion Source |
|---|
| Zinc chloride |
| Bismuth chloride |
| Zinc acetate |
| Aluminum sulfate |

The zinc salt was prepared via metathesis using the following procedure.

Compound 1 (200 mg) was dissolved in methanol (2 mL) to form a mixture. A 1 M NaOH solution (336 µL, 1.0 eq.) was then added to the mixture to form the 1:1 sodium salt of Compound 1. Zinc chloride (22.5 mg, 0.5 eq.) was dissolved in water (1 mL), and the resulting solution was added to the mixture, upon which a white solid precipitated out of solution. Additional water (1 mL) was added to the mixture and the reaction vessel was sealed with parafilm, after which the mixture was temperature cycled between ambient temperature and 40° C. in 4 hour cycles for 24 hours with agitation. The methanol was removed from the mixture via rotary evaporation and water (10 mL) was added to reduce the solubility. The resulting precipitate was isolated via Buchner filtration (Whatman Grade 1 filter paper, 0=55 mm) and washed with water (100 mL) to remove any remaining sodium chloride. The solid was dried on the filter paper, yielding a white powder (152.9 mg, 72%).

Figure 2:
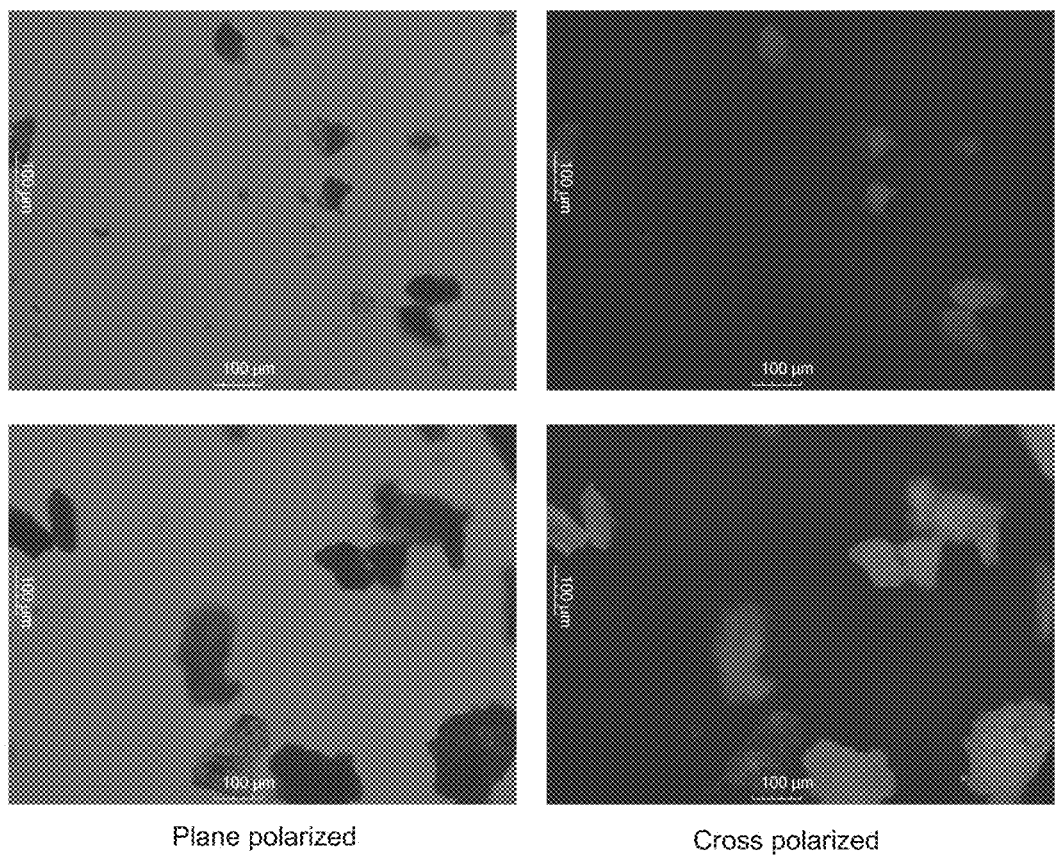
FIG. 2 shows PLM images of an amorphous zinc salt of Compound 1 prepared using zinc chloride as the counterion source.
Figure 3:
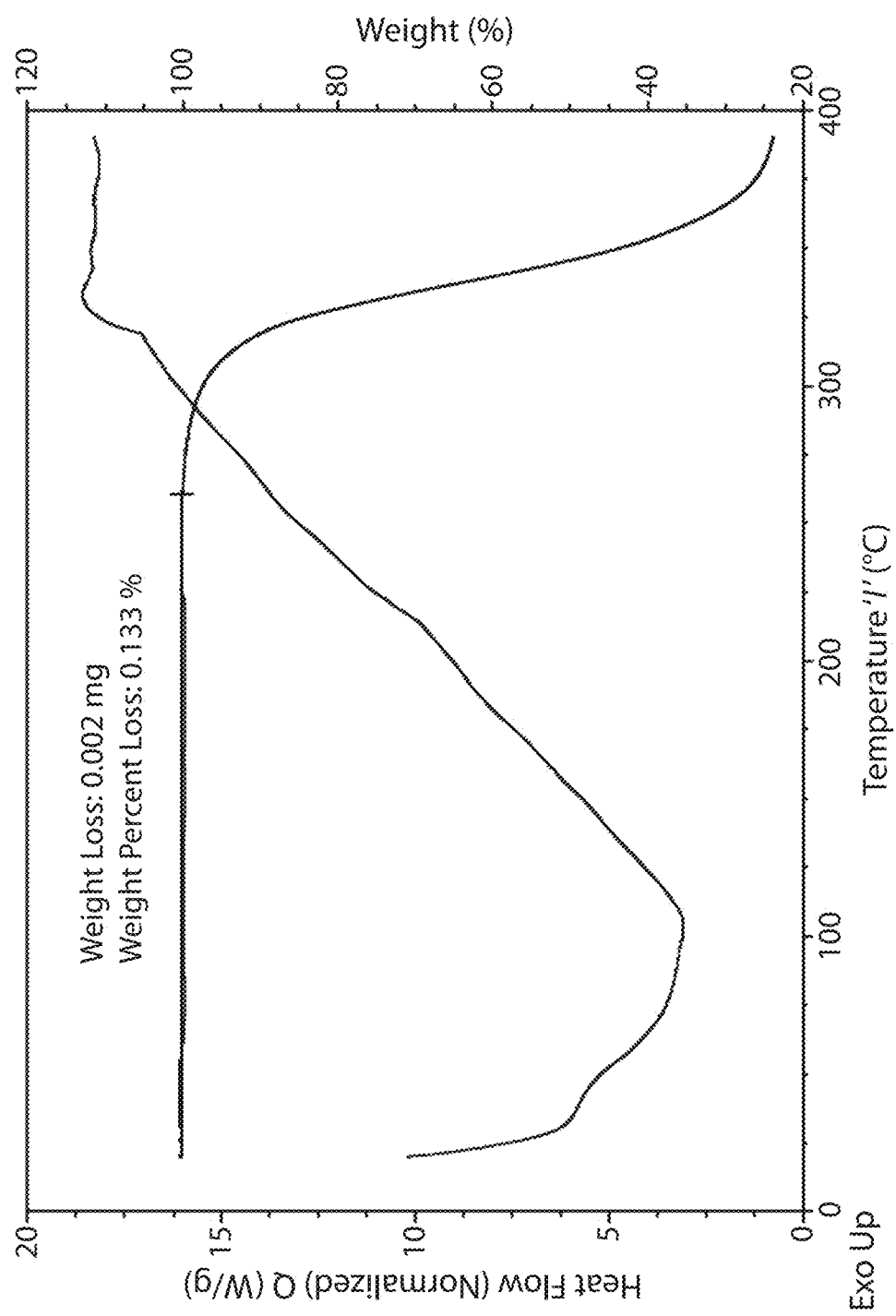
FIG. 3 is a TG/DTA thermogram of an amorphous zinc salt of Compound 1 prepared using zinc chloride as the counterion source.
Figure 4:
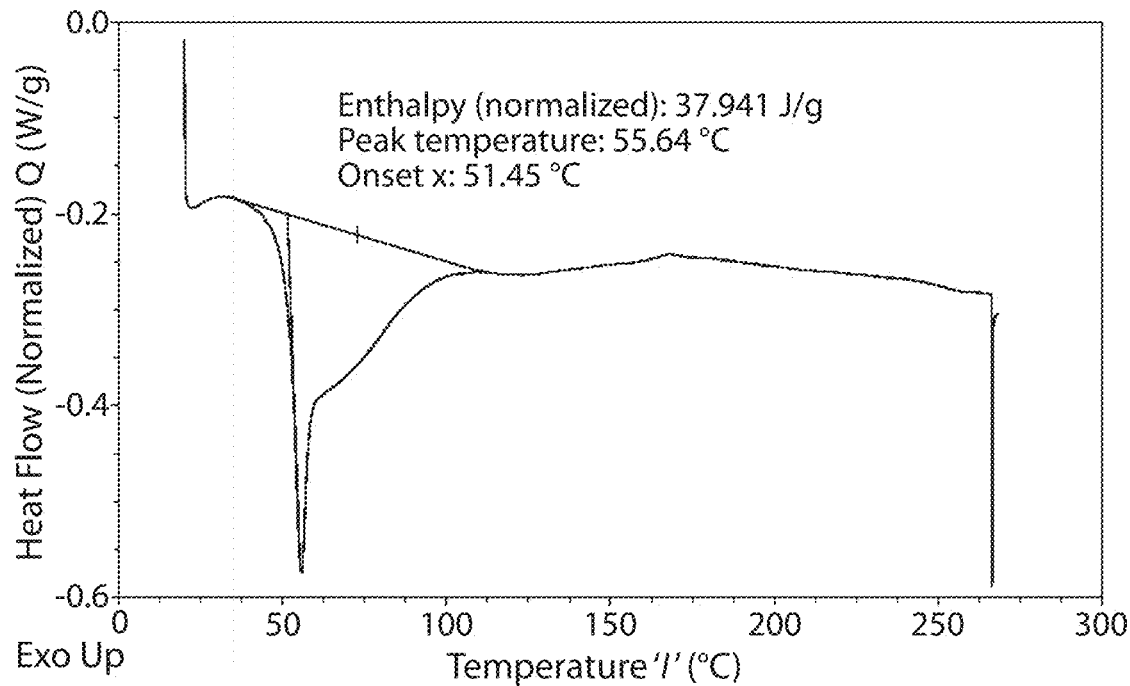
FIG. 4 shows DSC thermograms (top: first heat cycle; bottom: second heat cycle) of an amorphous zinc salt of Compound 1 prepared using zinc chloride as the counterion source.
Figure 4:
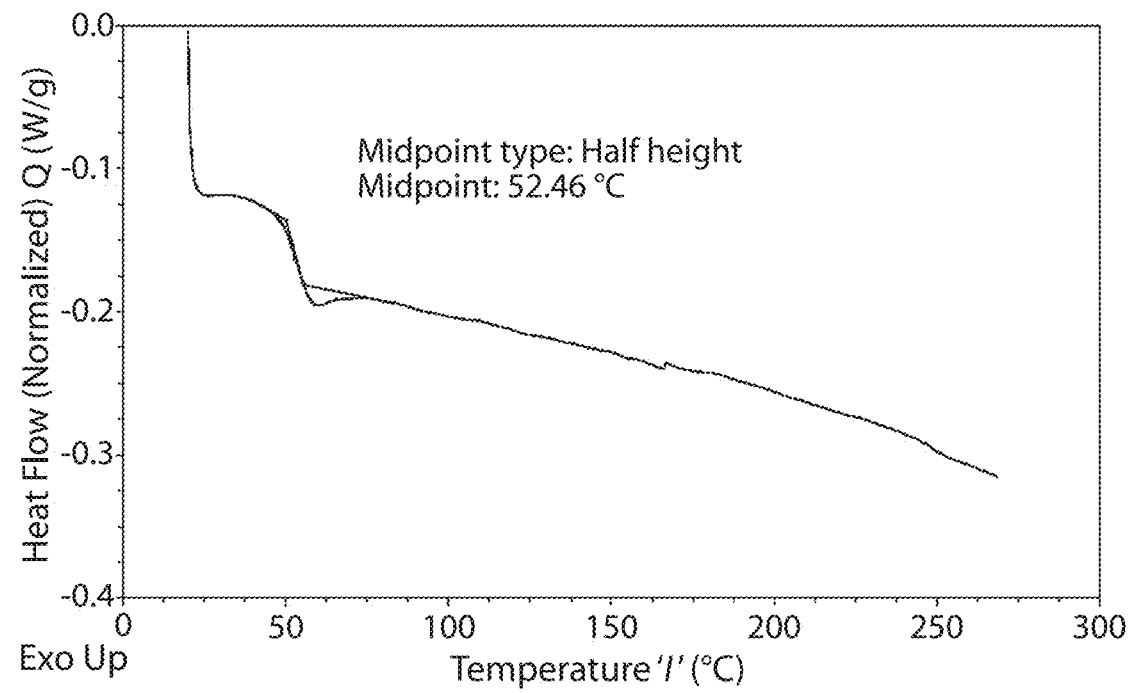
Figure 5:
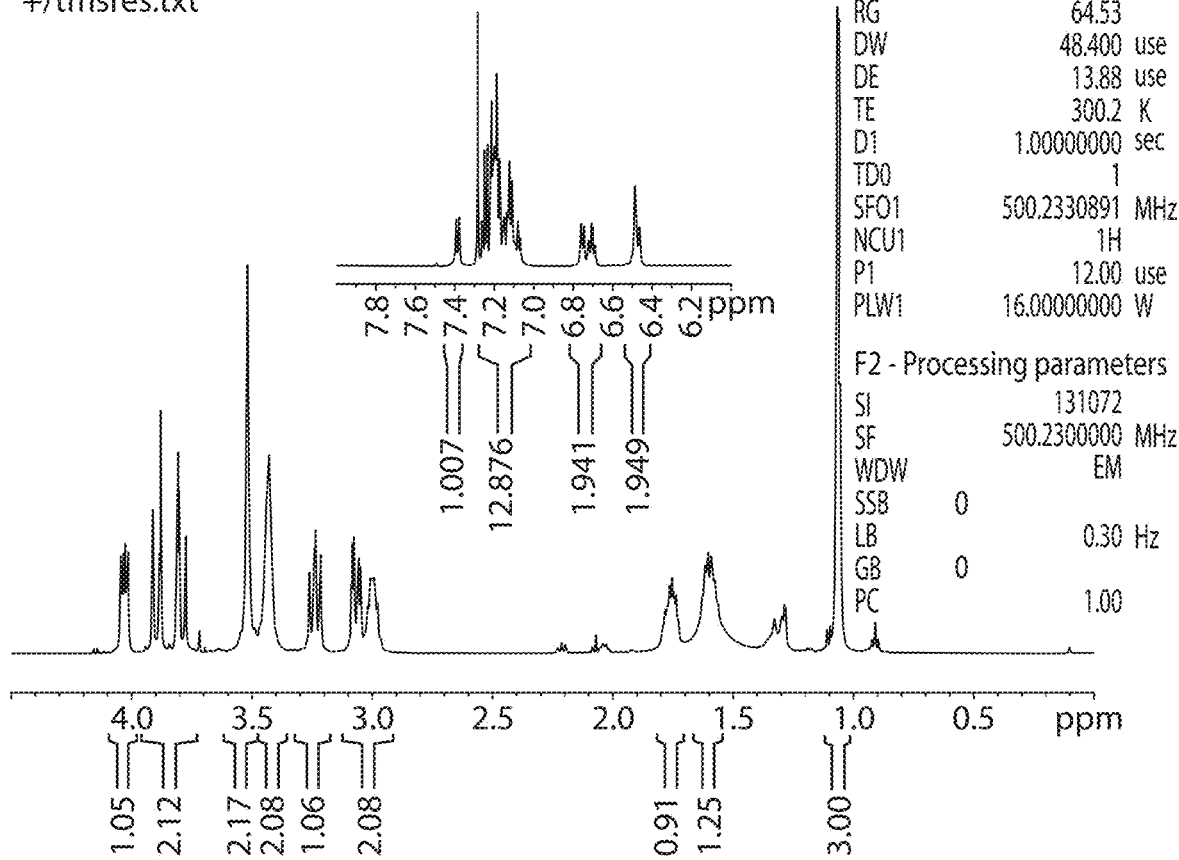
FIG. 5 is a $^1$H-NMR spectrum (solvent: $CDCl_3$) of an amorphous zinc salt of Compound 1 prepared using zinc chloride as the counterion source.
Figure 6:
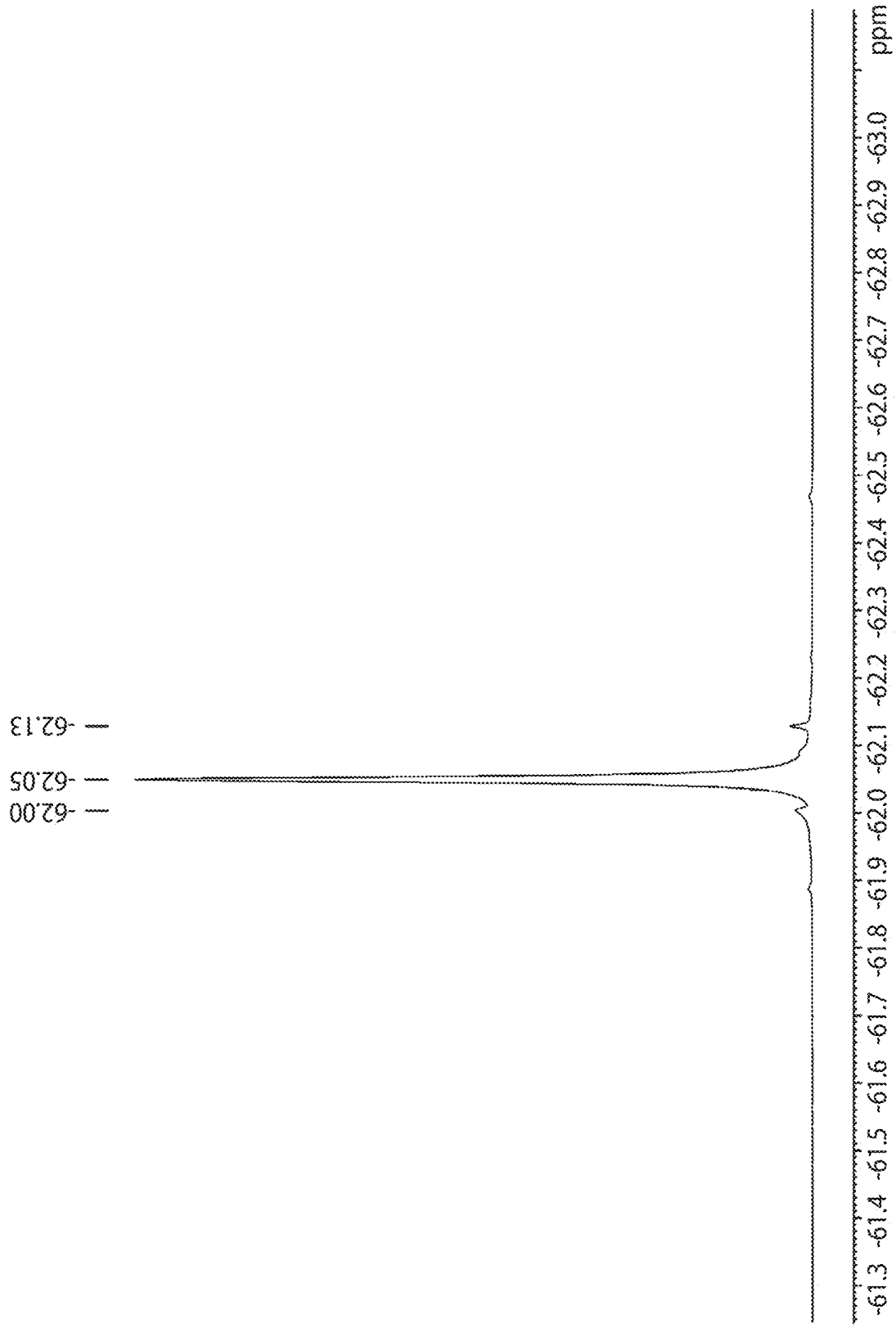
FIG. 6 is a $^{19}$F-NMR (solvent: $CDCl_3$) spectrum of an amorphous zinc salt of Compound 1 as the counterion source.

The material obtained via the above-described salt metathesis procedure was characterized by ICP, XRPD (FIG. 1), PLM (FIG. 2), TG/DTA (FIG. 3), DSC (FIG. 4), $^1$H-NMR (FIG. 5), and $^{19}$F-NMR (FIG. 6) following the methods described in Example 1. Characterization of the material yielded the following information:

- The material contained 5.27 wt. % zinc by ICP analysis. Stoichiometric salt is 9.9 wt. %, therefore there is approximately 0.51 eq. zinc (0.5 eq. expected).
- The material contained 0.19 wt. % sodium by ICP analysis. Stoichiometric salt is 3.7 wt. %, therefore approximately 5% of the material is the 1:1 sodium salt, and approximately 95% of the material is the 2:1 zinc salt.
- The material was amorphous by XRPD analysis.
- The material showed some birefringence by PLM analysis, with irregular morphology.
- There was minimal mass loss in the TG trace up to decomposition.
- By DSC, there was an endothermic event with an onset temperature of 51° C. in the first heat cycle, and a sharp event corresponding to glass transition with a midpoint temperature at 52° C. in the second heat cycle.
- The $^1$H-NMR spectrum was consistent with Compound 1.
- The $^{19}$F-NMR showed one main peak.
- The purity of the amorphous material, as determined by HPLC analysis, is shown in Table 8 below.

TABLE 8

Purity and stability of the zinc salt of Compound 1 prepared from zinc chloride

| Time (days) | Purity |
| --- | --- |
| 0 | 99.3% |
| 7 (stored at 40° C./75% RH) | 99.5% |
| 7 (stored at 80° C.) | 96.2% |

As shown in Table 8, the zinc salt prepared by the method described above is stable after one week of storage at 40° C./75% RH and at 80° C.

The zinc salt was also prepared using zinc acetate as the counterion source. Briefly, Compound 1 (78 mg) was dissolved in methanol (1.5 mL), and zinc acetate was dissolved in methanol/water (9:1; 1.5 mL), after which the two solutions thus obtained were combined to form a mixture. A white solid immediately formed and precipitated from solution. The sample was then cycled between ambient temperature and 40° C. for approximate 5 hours, after which a small amount of white solid remained undissolved. The solvent was then removed via rotary evaporation, and methanol (5 mL) was added to the solid. The cycling and solvent evaporation steps were repeated, then methanol/water (9:1; 5 mL) was added to the sample, and the cycling and solvent evaporation steps were repeated once more. The sample was subsequently frozen lyophilized overnight to remove water, after which a white solid was obtained.

The aluminum salt was prepared via metathesis using the following procedure. Compound 1 (200 mg) was dissolved in methanol (2 mL). The sodium salt was prepared by adding a 1 M NaOH stock solution (336 µL, 1.0 eq.). The methanol was removed via rotary evaporation. Aluminum sulfate and water (2 mL) were added and the sample temperature cycled between ambient and 40° C. in 4-hour cycles for 24 hours. The solid was isolated via centrifugation. Water (3 mL) was added and the slurry agitated at ambient temperature for 18 hours. The solid was filtered using a Buchner funnel (Whatman Grade 1 filter paper, 0=42.5 mm) and washed with water (100 mL) before being dried on the filter paper for 10 minutes. The solid was dried under vacuum at ambient temperature for ca. 2 hours, yielding a white powder (128.7 mg, 61%).

Example 3. FTIR Analysis

Study

Figure 7:
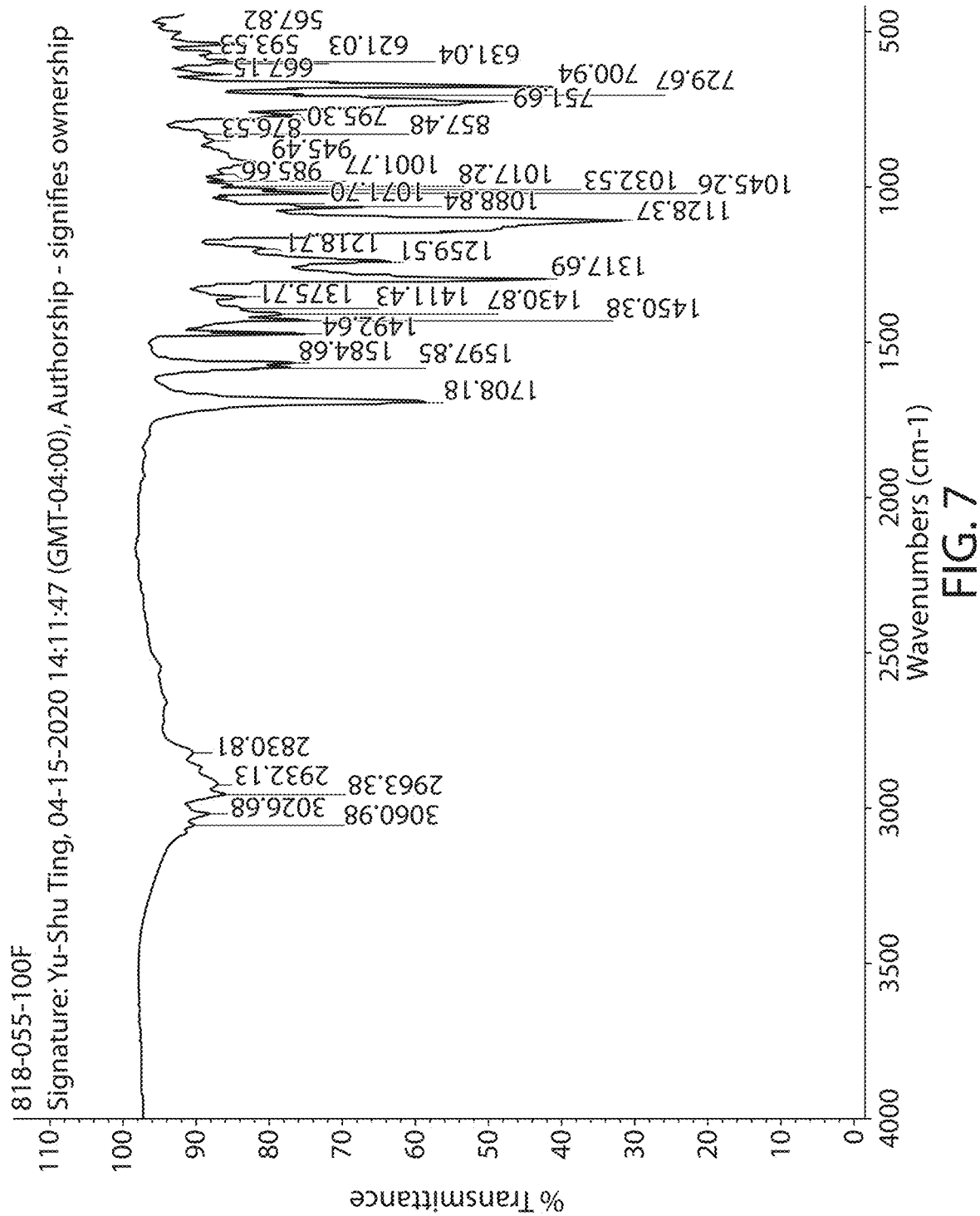
FIG. 7 is a FTIR spectrum of a free form of Compound 1.
Figure 8:
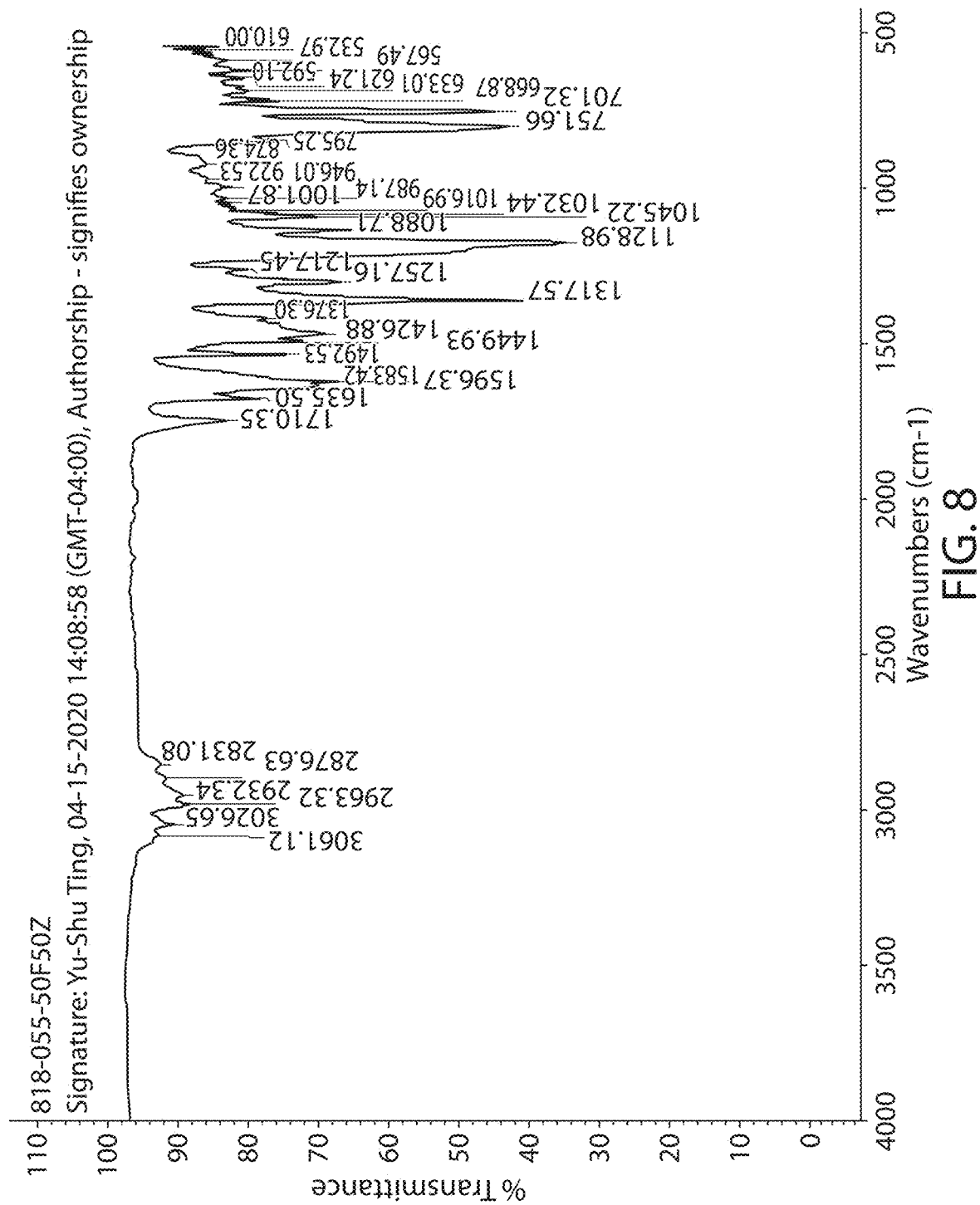
FIG. 8 is a FTIR spectrum of a 1:1 (w/w) mixture of a free form of Compound 1 and an amorphous zinc salt of Compound 1.

Stock solutions of the free compound and zinc salt of Compound 1 in CHCl$_3$ were prepared. The free form of Compound 1 (50 mg) was diluted to 10 mL with CHCl$_3$ in a volumetric flask. The zinc salt of Compound 1 (50 mg) was also diluted to 10 mL with CHCl$_3$ in a separate volumetric flask. A FTIR spectrum was taken of the free form of Compound 1 (see FIG. 7), and of the zinc salt form of Compound 1 (see FIG. 9) according to the FTIR method described in Example 1. FTIR spectra were then taken of samples with increasing concentrations of the zinc salt of Compound 1, such as:

- a 1:1 (w/w) mixture of the free form: zinc salt of Compound 1 (mixture of the free form stock solution (500 µL) with the zinc salt stock solution (500 µL)) (see FIG. 8);
- a 1:4 (w/w) mixture of the free form: zinc salt of Compound 1 (mixture of the free form stock solution (200 µL) with the zinc salt stock solution (800 µL));
- a 1:9 (w/w) mixture of the free form: zinc salt of Compound 1 (mixture of the free form stock solution (100 µL) with the zinc salt stock solution (900 µL));
- and a 5:95 (w/w) mixture of the free form: zinc salt of Compound 1 (mixture of the free form stock solution (50 µL) with the zinc salt stock solution (950 µL)).

Figure 10:
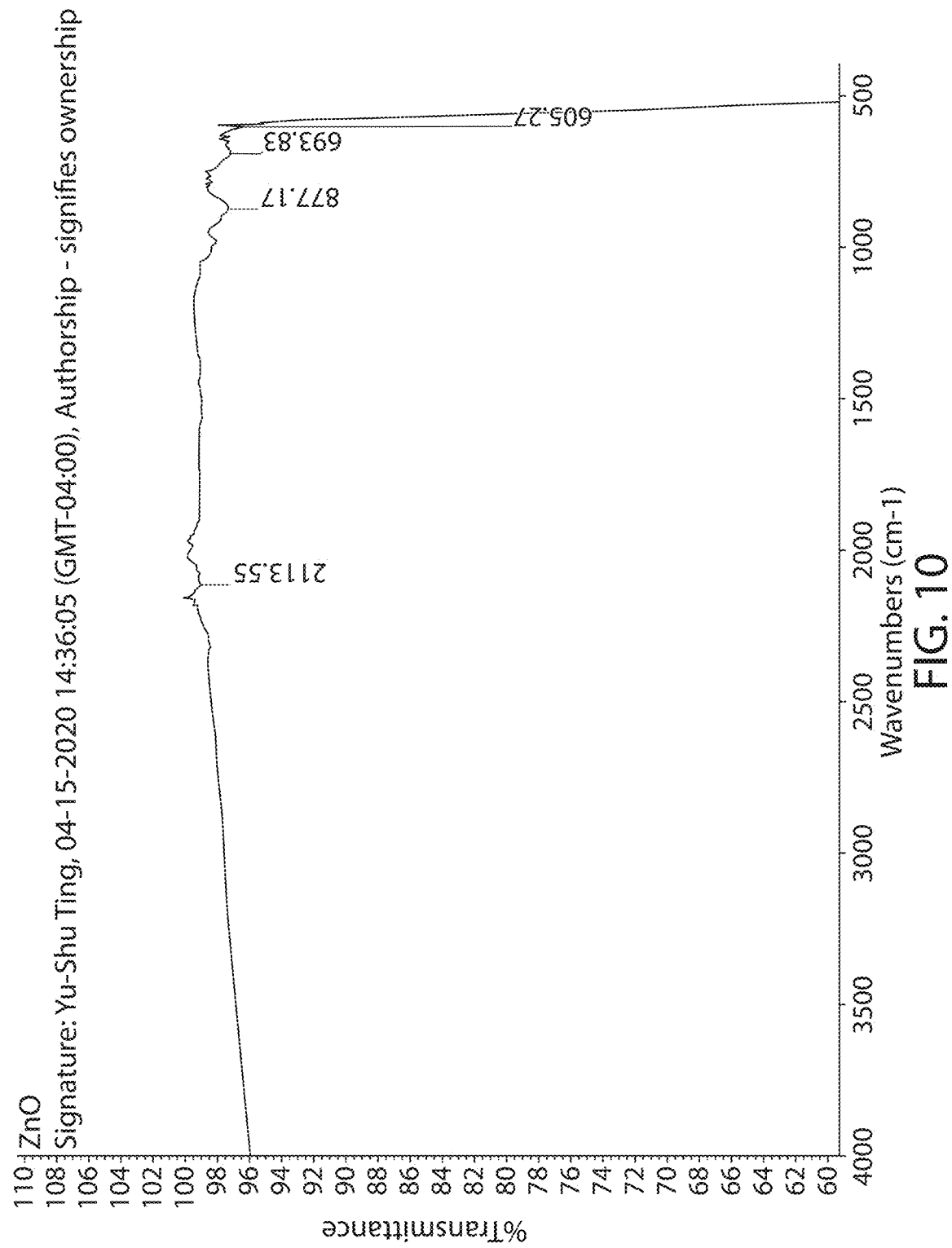
FIG. 10 is a FTIR spectrum of ZnO.
Figure 11:
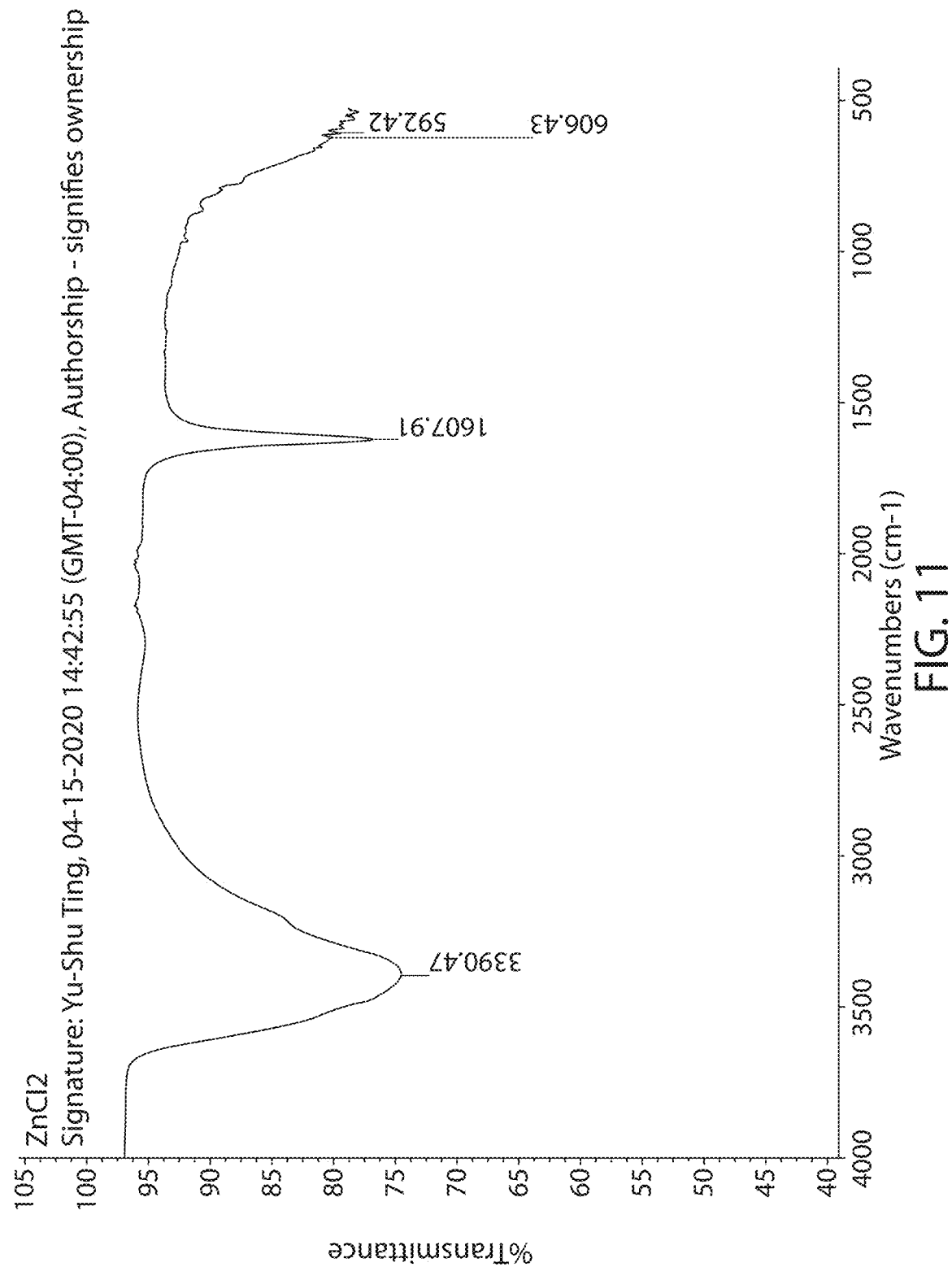
FIG. 11 is a FTIR spectrum of $ZnCl_2$.

The spectra were compared with each other as well as FTIR spectra of ZnO (FIG. 10) and ZnCl$_2$ (FIG. 11).

Figure 9:
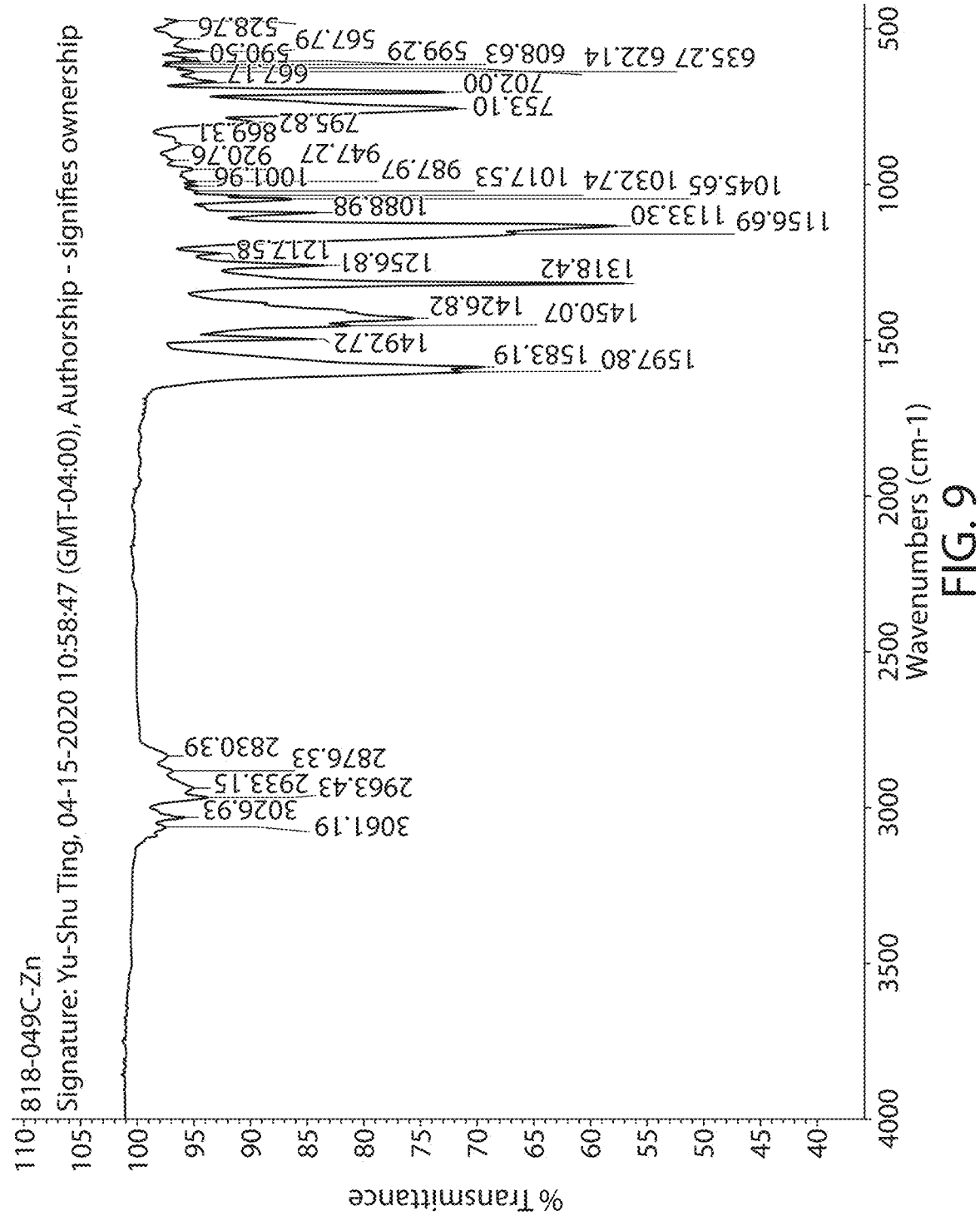
FIG. 9 is a FTIR spectrum of an amorphous zinc salt of Compound 1.

The free form of Compound 1 exhibited a distinct, characteristic peak at about 1710 cm$^{-1}$ (see FIG. 7) which is not present in the zinc salt spectrum (see FIG. 9). The peak at 1710 cm$^{-1}$ was observed to shrink as the percentage of the free form decreased. Additionally, a broad peak at about 1590 cm$^{-1}$ was observed with low intensity in the free compound, but increased in intensity as the concentration of the zinc salt increased.

The zinc salt is evidenced by the disappearance of the IR peak at 1710 cm$^{-1}$, presumably, due to coordination of the carboxylate carbonyl with zinc. Furthermore, the zinc salt does not contain peaks found in the IR spectrum of ZnO (characterized by a distinct, large, broad band starting at 605 cm$^{-1}$ to <500 cm$^{-1}$) or ZnCl$_2$ (characterized by a distinct broad peak at 3386 cm$^{-1}$), thus further demonstrating the zinc salt is not simply a mixture of the free compound and inorganic zinc.

Other Embodiments

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

While the methods have been described in conjunction with various embodiments and examples, it is not intended that the methods be limited to such embodiments or examples. On the contrary, the present disclosure encompasses various alternatives, modifications, and equivalents, as will be appreciated by those of skill in the art.

While the methods have been particularly shown and described with reference to specific illustrative embodiments, it should be understood that various changes in form and detail may be made without departing from the spirit and scope of the present disclosure. Therefore, all embodiments that come within the scope and spirit of the present disclosure, and equivalents thereto, are intended to be claimed. The claims, descriptions and diagrams of the methods, systems, and assays of the present disclosure should not be read as limited to the described order of elements unless stated to that effect. This application claims the benefit of U.S. provisional Ser. No. 62/947,968, filed Dec. 13, 2019, which is incorporated herein in its entirety.

The invention claimed is:

1. A method of treating cancer in a subject in need thereof, the method comprising administering to the subject an effective amount of a zinc salt of 2-[3-[(3R)-3-[[2-chloro-3-(trifluoromethyl)phenyl]methyl-(2,2-diphenylethyl)amino]butoxy]phenyl]acetic acid (Compound 1), wherein the zinc salt is a 2:1 (Compound 1:zinc) salt and wherein the cancer is selected from the group consisting of breast cancer, endometrial cancer, colon cancer, renal cell cancer, lung cancer, hepatocellular carcinoma, gastric cancer, ovarian cancer, pancreatic cancer, esophageal cancer, prostate cancer, sarcoma, bladder cancer, head and neck cancer, glioblastoma, diffuse large B-cell lymphoma, leukemia, and melanoma.

2. The method of claim 1, wherein the method comprises orally administering the zinc salt formulated as a pharmaceutical composition for oral administration comprising (i) the zinc salt of 2-[3-[(3R)-3-[[2-chloro-3-(trifluoromethyl)phenyl]methyl-(2,2-diphenylethyl)amino]butoxy]phenyl]acetic acid (Compound 1), wherein the zinc salt is a 2:1 (Compound 1:zinc) salt, and (ii) a pharmaceutically acceptable excipient.

3. The method of claim 2, wherein the pharmaceutical composition is in the form of an emulsion, an aqueous suspension, a dispersion, or a solution.

4. The method of claim 3, wherein the pharmaceutical composition is in unit dosage form.

5. The method of claim 4, wherein the pharmaceutical composition is a unit dosage form comprising a capsule or a tablet.

6. The method of claim 4, wherein the pharmaceutical composition is a unit dosage form comprising a solution of the zinc salt.

7. The method of claim 1, wherein the cancer is metastatic cancer.

8. The method of claim 7, wherein the effective amount comprises an amount effective to suppress metastatic colonization of said cancer.

9. The method of claim 1, wherein the subject has a cancer that has failed to respond to a previously administered immunotherapy.

10. The method of claim 1, wherein the subject has a cancer resistant to an immunotherapy.

* * * * *